United States Patent [19]

Condon et al.

[11] Patent Number: 5,424,280
[45] Date of Patent: Jun. 13, 1995

[54] ARYLOXYBENZENE HERBICIDAL AGENTS

[75] Inventors: Michael E. Condon, Lawrenceville; Alvin D. Crews, Jr., Voorhees, both of N.J.

[73] Assignee: American Cyanamid Company, Wayne, N.J.

[21] Appl. No.: 133,698

[22] Filed: Oct. 7, 1993

[51] Int. Cl.⁶ .................... C07C 205/35; A01N 39/04
[52] U.S. Cl. ..................... 504/316; 504/258; 504/282; 504/315; 504/324; 504/338; 504/352; 546/300; 548/370.1; 548/367.1; 548/365.7; 548/366.4; 548/368.1; 568/586; 560/9; 560/21; 562/430; 562/435; 562/868; 564/166
[58] Field of Search ............... 560/21; 558/424; 504/316, 311

[56] References Cited

U.S. PATENT DOCUMENTS 4,364,875 12/1982 Sehring et al. ............... 560/21
4,376,646 3/1983 Rohr et al. ................... 564/49

FOREIGN PATENT DOCUMENTS

98569A2 1/1984 European Pat. Off. .
129321A2 12/1984 European Pat. Off. .

Primary Examiner—Glennon H. Hollrah
Assistant Examiner—Scott C. Rand
Attorney, Agent, or Firm—Peggy A. Climenson

[57] ABSTRACT

There are provided aryloxybenzene compounds of formula I

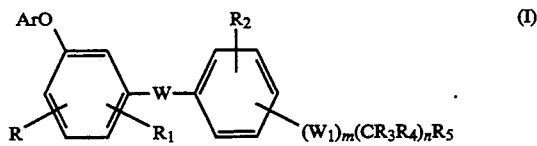

Further provided are compositions and methods comprising those compounds for the control of undesirable plant species.

2 Claims, No Drawings

ARYLOXYBENZENE HERBICIDAL AGENTS

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

It is an object of the present invention to provide compounds which are highly effective for controlling undesirable plant species.

It is also an object of the present invention to provide a method for controlling undesirable plant species.

These and other objects of the present invention will become more apparent from the detailed description thereof set forth below.

SUMMARY OF THE INVENTION

The present invention describes aryloxybenzene compounds which are useful as herbicidal agents.

The aryloxybenzene compounds of the present invention have the following structural formula I:

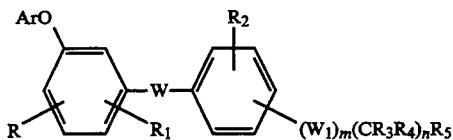

wherein
Ar is

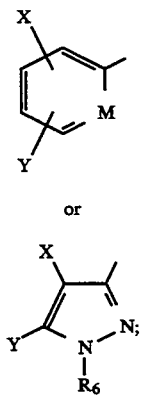

M is N or CZ;
X, Y and Z are each independently hydrogen, halogen, $C_1$–$C_4$alkyl, $C_1$–$C_4$haloalkyl, $C_1$–$C_4$haloalkoxy, cyano, nitro or $S(O)_pR_7$ with the proviso that X, Y and Z cannot simultaneously be nitro;
p is an integer of 0, 1 or 2;
$R_7$ is $C_1$–$C_4$alkyl or $C_1$–$C_4$haloalkyl;
$R_6$ is $C_1$–$C_4$alkyl;
W and $W_1$ are each independently O, S or $NR_8$;
$R_8$ is hydrogen or $C_1$–$C_4$alkyl;
m is an integer of 0 or 1;
R is nitro, halogen, cyano, $C_1$–$C_4$alkylsulfonyl or $C_1$–$C_4$haloalkylsulfonyl;
$R_1$ is hydrogen, halogen or nitro;
$R_2$ is hydrogen, halogen, $C_1$–$C_4$alkyl or $C_1$–$C_4$haloalkyl;
$R_3$ and $R_4$ are each independently hydrogen, $C_1$–$C_4$alkyl, or $C_1$–$C_4$haloalkyl, and when taken together $R_3$ and $R_4$ may form a ring in which $R_3R_4$ are represented by —$(CH_2)_q$—where q is an integer of 2, 3, 4 or 5;
n is an integer of 0, 1, 2, 3, 4 or 5;
$R_5$ is cyano, $C(O)R_9$, $C(Q)R_{10}$, $CH_2OC(O)R_{11}$, $CH_2OR_{10}$, $CH(OR_{12})_2$, $N(R_{10})SO_2R_{13}$ or $C_2$–$C_6$ alkenyl substituted with one $CO_2R_{11}$ group;
$R_9$ is OH, $OR_{14}$, $NR_{15}R_{16}$ or $N(R_{10})SO_2R_{13}$;
Q is O, $NOC(R_3R_4)CO_2R_{12}$ or $NOR_{11}$;
$R_{10}$ is hydrogen or $C_1$–$C_4$alkyl optionally substituted with $C_1$–$C_4$alkoxy;
$R_{11}$ is hydrogen, $C_1$–$C_4$alkyl, benzyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;
$R_{12}$ is $C_1$–$C_4$alkyl, —$CH_2$—$CH_2$—$CH_2$— or $CH_2$—$CH_2$—$CH_2$—$CH_2$—;
$R_{13}$ is $C_1$–$C_4$alkyl, $C_1$–$C_4$haloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;
$R_{14}$ is $C_1$–$C_6$alkyl optionally substituted with $C_1$–$C_4$alkoxy, $C_1$–$C_4$alkylthio, halogen, hydroxy, $C_3$–$C_6$cycloalkyl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups,
$C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups,
$C_3$–$C_6$alkynyl optionally substituted with $C_1$–$C_4$alkoxy or halogen,
$C_3$–$C_6$cycloalkyl,
$N=C(R_3R_4)$,
$C(R_3R_4)CO_2R_{10}$ or
an alkali metal, alkaline earth metal, manganese, copper, zinc, cobalt, silver, nickel, ammonium or organic ammonium cation; and
$R_{15}$ and $R_{16}$ are each independently hydrogen, $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;
provided that when R is halogen, $R_1$ is hydrogen, $W_1$ is $NR_8$ and n is 0 then $R_5$ must be other than $C(O)NR_{15}R_{16}$.

This invention also relates to compositions containing those compounds and methods for using those compounds and compositions. Advantageously, it has been found that the aryloxybenzene compounds of the present invention, and compositions containing them, are effective herbicidal agents for the control of undesirable plant species. The compounds of the present invention are especially useful for the postemergence control of undesirable plant species.

DETAILED DESCRIPTION OF THE INVENTION

Advantageously, the present invention provides a method for controlling undesirable plant species by applying to the foliage of said plants or to the soil or water containing seeds or other propagating organs thereof, a herbicidally effective amount of a formula I, aryloxybenzene compound.

The present invention also provides a method for the control of undesirable plant species in transplanted rice by applying to the soil or water containing seeds or other propagating organs of said undesirable plant species, after the rice has been transplanted, a herbicidally effective amount of a formula I, aryloxybenzene compound.

The aryloxybenzene compounds of the present invention have the following structural formula I:

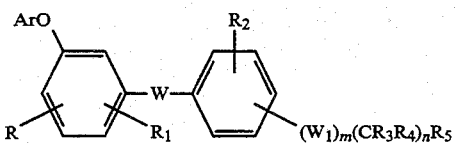
(I)

wherein Ar, W, $W_1$, m, n, R, $R_1$, $R_2$, $R_3$, $R_4$ and $R_5$ are as described hereinabove for formula I.

Preferred formula I aryloxybenzene compounds of the present invention are those wherein Ar is

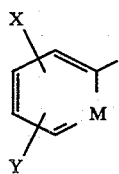

or

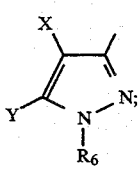

M is N or CZ;
X, Y and Z are each independently hydrogen, halogen, $C_1$–$C_4$haloalkyl or $S(O)_pR_7$;
p is an integer of 0, 1 or 2;
$R_7$ is $C_1$–$C_4$alkyl or $C_1$–$C_4$haloalkyl;
$R_6$ is $C_1$–$C_4$alkyl;
W is O or NH;
$W_1$ is O;
m is an integer of 0 or 1;
R is nitro;
$R_1$ is hydrogen, halogen or nitro;
$R_2$ is hydrogen;
$R_3$ and $R_4$ are each independently hydrogen or $C_1$–$C_4$alkyl;
n is an integer of 0, 1, 2, 3, 4 or 5;
$R_5$ is $C(O)R_9$;
$R_9$ is OH or $OR_{14}$; and
$R_{14}$ is $C_1$–$C_6$alkyl, $C_3$–$C_6$alkenyl, $C_3$–$C_6$alkynyl or an alkali metal, alkaline earth metal, ammonium or tri($C_1$–$C_6$alkyl)ammonium cation.

More preferred formula I herbicidal agents of the present invention are those having the following structural formula II

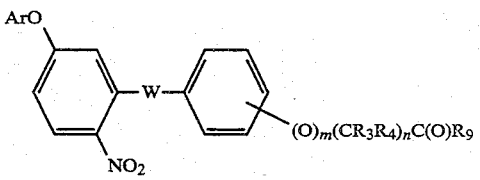
(II)

wherein
Ar is

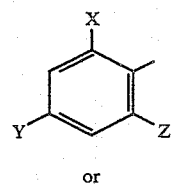

or

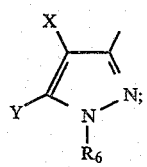

Y is halogen, $CF_3$ or $S(O)_pR_7$;
X is hydrogen or halogen;
Z is halogen;
p is an integer of 0, 1 or 2;
$R_7$ is $C_1$–$C_4$alkyl or $C_1$–$C_4$haloalkyl;
$R_6$ is $C_1$–$C_4$alkyl;
W is O or NH;
m is an integer of 0 or 1;
$R_3$ and $R_4$ are each independently hydrogen or $C_1$–$C_4$alkyl;
n is an integer of 0 or 1;
$R_9$ is OH or $OR_{14}$; and
$R_{14}$ is $C_1$–$C_6$alkyl or an alkali metal, alkaline earth metal, ammonium or tri($C_1$–$C_6$alkyl)ammonium cation.

Aryloxybenzene compounds of the present invention which are particularly effective herbicidal agents include
methyl {o-{5-[(2-chloro-α,α,α,6-tetrafluoro-p-tolyl)oxy]-2-nitrophenoxy}phenoxy}acetate;
{o-{5-[(2-chloro-α,α,α,6-tetrafluoro-p-tolyl)oxy]-2-nitrophenoxy}phenoxy}acetic acid;
methyl {o-[5-(2,4-dichlorophenoxy)-2-nitrophenoxy]phenoxy}acetate;
methyl {o-{5-[(2-chloro-α,α,α,-trifluoro-p-tolyl)oxy]-2-nitrophenoxy}phenoxy}acetate;
methyl p-{5-[(2-chloro-α,α,α,6-tetrafluoro-p-tolyl)oxy]-2-nitrophenoxy}benzoate;
methyl {o-{5-{[4-chloro-1-methyl-5-(trifluoromethyl)-pyrazol-3-yl]oxy}-2-nitrophenoxy}phenoxy}acetate;
methyl {p-{5-[(2-chloro-α,α,α,6-tetrafluoro-p-tolyl)oxy]-2-nitroanilino}phenoxy}acetate;
propyl {o-[5-(2,4-dichlorophenoxy)-2-nitrophenoxy]phenoxy}acetate;
methyl {o-{2-nitro-5-[(α,α,α,2-tetrafluoro-p-tolyl)oxy]phenoxy}phenoxy}acetate;
methyl {o-{5-{[1-methyl-5-(trifluoromethyl)pyrazol-3-yl]oxy}-2-nitrophenoxy}phenoxy}acetate;
{o-{5-[2-chloro-4-(methylsulfinyl)phenoxy]-2-nitrophenoxy}phenoxy}acetic acid; and methyl {o-{5-[2-chloro-4-(methylsulfinyl)phenoxy]-2-nitrophenoxy}phenoxy}acetate, among others.

Exemplary of halogen hereinabove are fluorine chlorine, bromine and iodine. The term "$C_1$-$C_4$haloalkyl" is defined as a $C_1$-$C_4$alkyl group substituted with one or more halogen atoms. In formulas I and II above, alkali metals include: sodium, potassium and lithium. Alkaline earth metals of formulas I and II include magnesium and calcium. Further, the term "organic ammonium" is defined as a group consisting of a positively charged nitrogen atom joined to from one to four aliphatic groups, each containing from one to sixteen carbon atoms.

Advantageously, it has been found that the formula I compounds of the present invention are especially useful for the postemergence control of undesirable plant species.

Certain aryloxybenzene compounds of formula I wherein R is $NO_2$, $R_2$ is hydrogen, W is O, and $R_5$ is $CO_2R_{14}$ may be prepared by reacting an aryl 3,4-dinitrophenyl ether of formula III with a substituted phenol of formula IV and a base such as potassium carbonate. The reaction scheme is shown in Flow Diagram I.

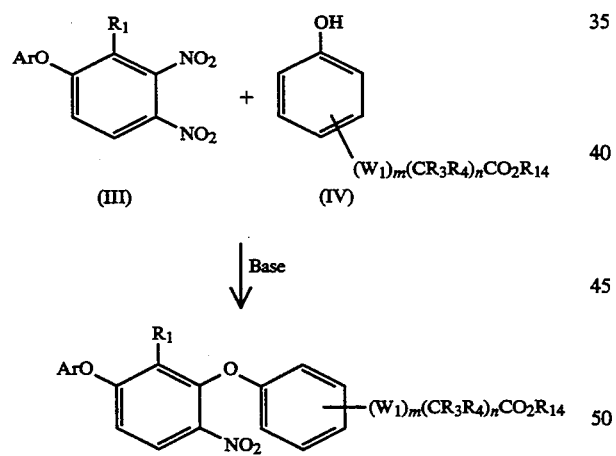

Certain herbicidal aryloxybenzene compounds of formula I wherein R is $NO_2$, $R_2$ is hydrogen, W and $W_1$ are O, m is 1, and $R_5$ is $CO_2R_{14}$ may be prepared by reacting an aryl 3,4-dinitrophenyl ether of formula III with a methoxyphenol of formula V and a base such as potassium carbonate to form a first intermediate of formula VI. Said first intermediate is then reacted with boron tribromide to form a second intermediate of formula VII which is reacted with a haloalkylcarboxylate of formula VIII and a base such as potassium carbonate to form the desired bis(aryloxy)benzene compound. The reaction scheme is shown in Flow Diagram II.

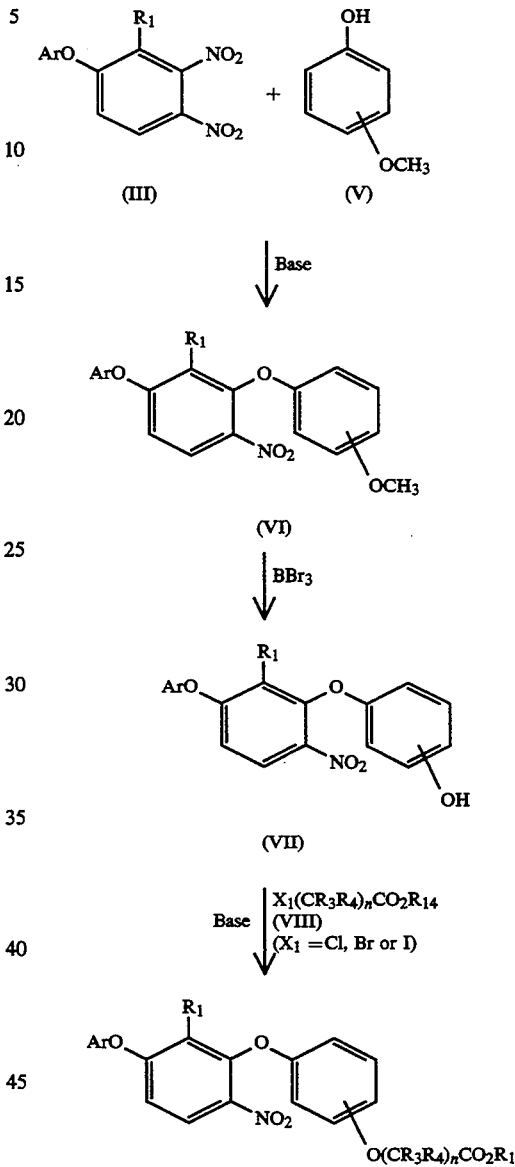

Alternatively, (pyridyloxy)(phenoxy)benzene compounds of this invention may be prepared by reacting a 2-fluoro-4-(methoxymethoxy)benzene of formula IX with a substituted phenol of formula X and a base such as potassium carbonate to form an intermediate of formula XI. The formula XI intermediate is then reacted with an acid such as hydrochloric acid to form an intermediate of formula XII which is reacted with a substituted pyridine of formula XIII and a base such as potassium carbonate to obtain the desired (pyridyloxy)(phenoxy)benzene compound. The reaction scheme is shown in Flow Diagram III.

5,424,280
FLOW DIAGRAM III
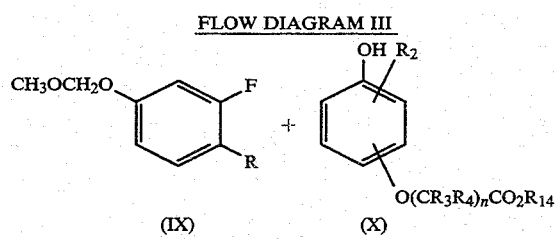
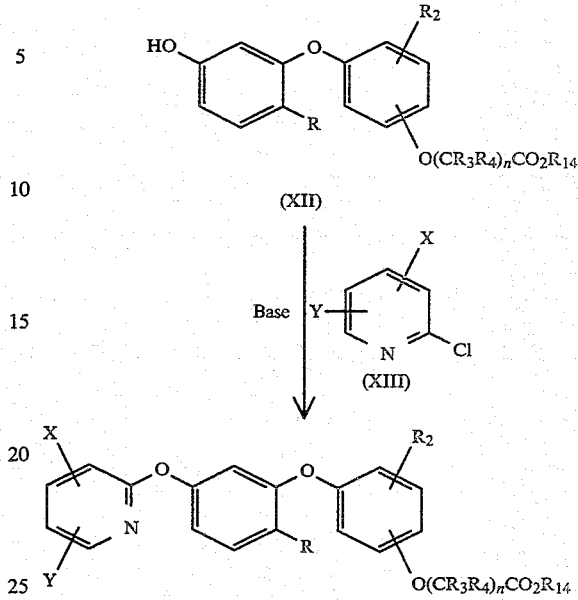
Advantageously, certain phenoxybenzene compounds of formula I may be prepared as shown below in Flow Diagram IV.
FLOW DIAGRAM IV
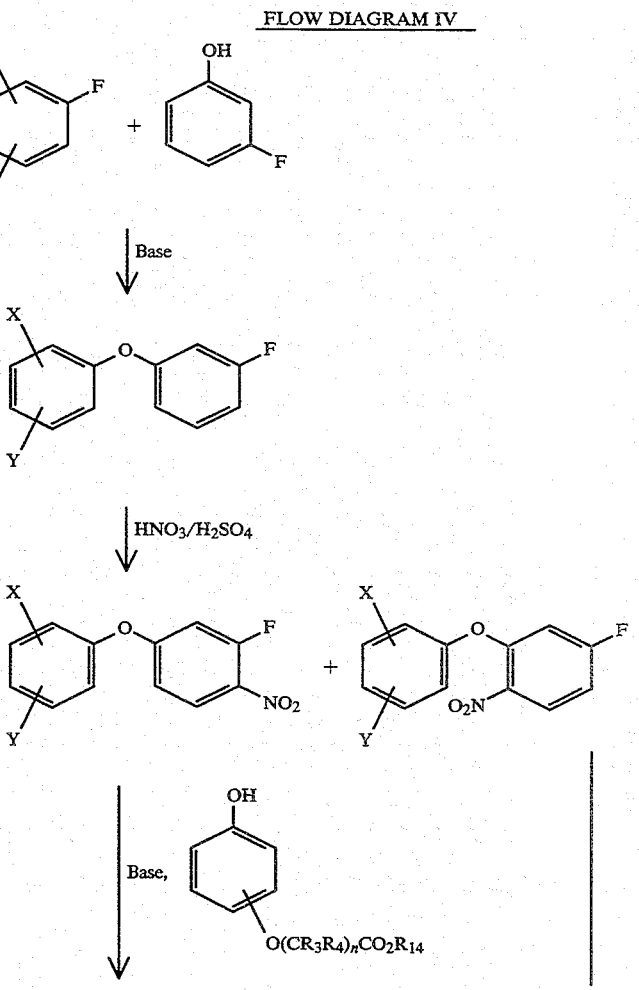

FLOW DIAGRAM IV -continued

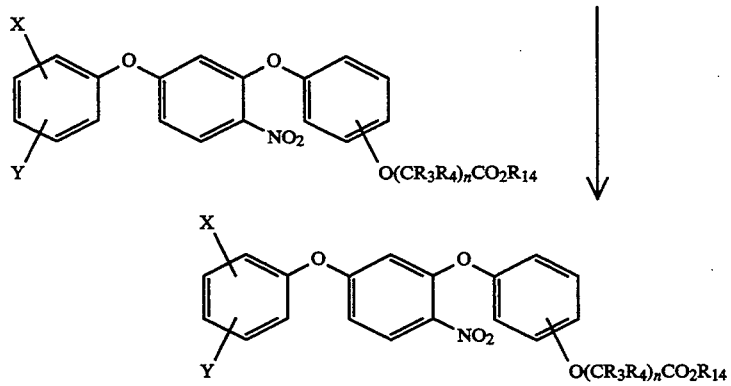

20

Similarly, (anilino)(phenoxy)benzene compounds may be prepared as shown below in Flow Diagram. V.

FLOW DIAGRAM V

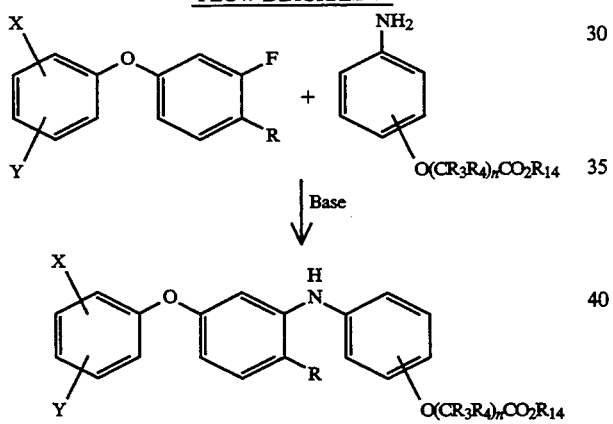

Other aryloxybenzene compounds of formula I may be prepared by reacting 2,4-difluoronitrobenzene with a substituted phenol of formula X and a base such as potassium carbonate to form an intermediate of formula XIV. The formula XIV intermediate is then reacted with a hydroxyaryl compound of formula XV and a base such as potassium carbonate to form the desired compound. The reaction scheme is shown in Flow Diagram VI.

FLOW DIAGRAM VI

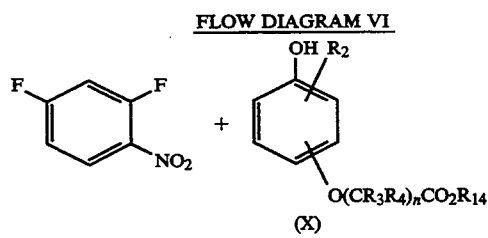

-continued
FLOW DIAGRAM VI

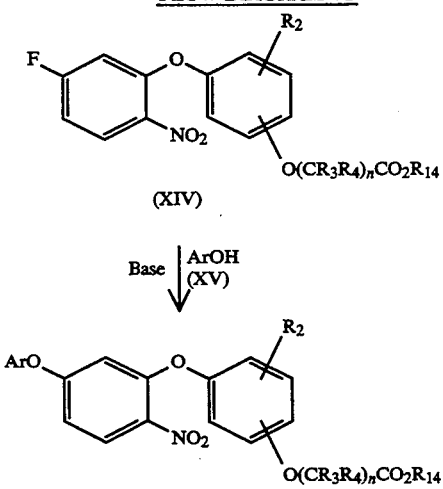

Alternatively, certain aryloxybenzene compounds may be prepared as shown below in Flow Diagram VII.

FLOW DIAGRAM VII

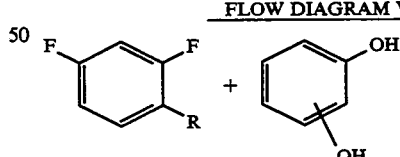

FLOW DIAGRAM VII

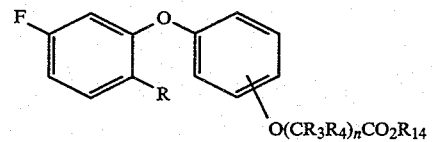

↓ Base | ArOH

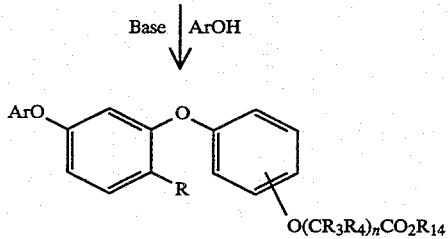

Certain compounds of formula I wherein $W_1$ is $NR_8$ may be prepared as shown below in Flow Diagram VIII.

FLOW DIAGRAM VIII

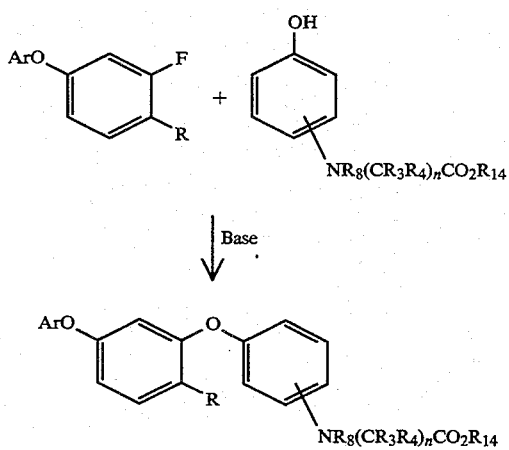

↓ Base

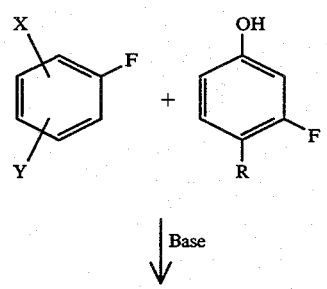

Similarly, certain phenoxybenzene compounds of formula I may be prepared as shown below in Flow Diagram IX.

FLOW DIAGRAM IX

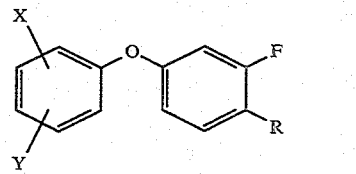

↓ Base

FLOW DIAGRAM IX -continued

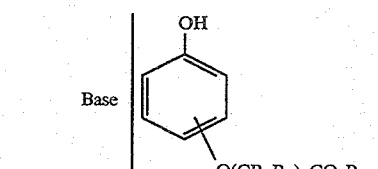

↓ Base

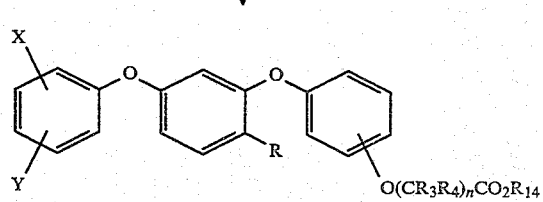

Certain compounds of formula I wherein $R_9$ is $NR_{15}R_{16}$ may be prepared as shown below in Flow Diagram X.

FLOW DIAGRAM X

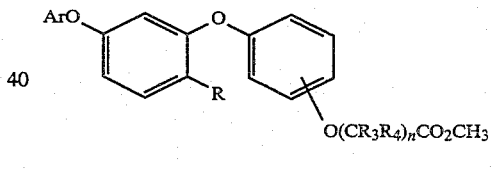

↓ 1. Base
2. $SOCl_2$

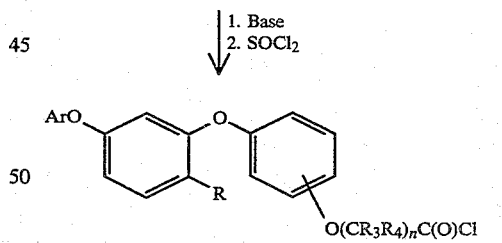

↓ $NHR_{15}R_{16}$, Base

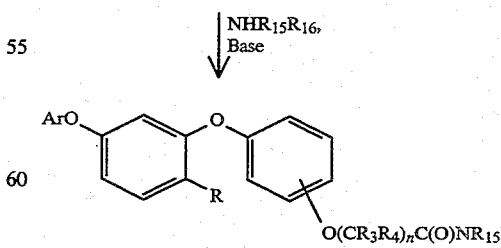

Similarly, certain aryloxybenzene compounds of formula I wherein $R_9$ is $N(R_{10})SO_2R_{13}$ may be prepared as shown below in Flow Diagram XI.

FLOW DIAGRAM XI

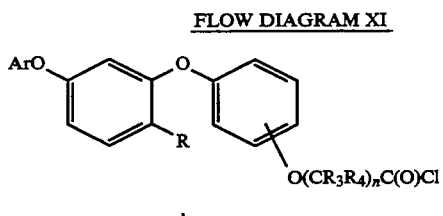

Base | NH(R$_{10}$)SO$_2$R$_{13}$

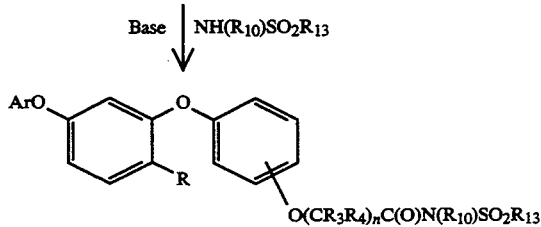

Other formula I compounds wherein R$_5$ is C(O)R$_{10}$ may be prepared as shown below in Flow Diagram XII.

FLOW DIAGRAM XII

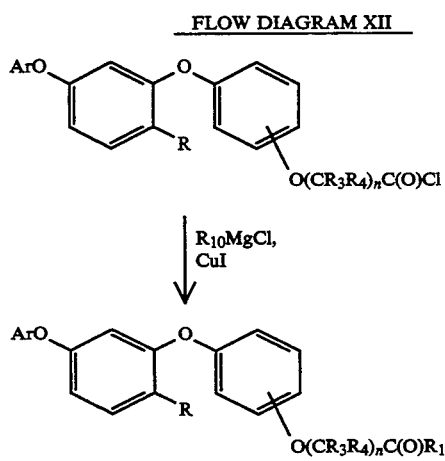

Certain aryloxybenzene compounds wherein R$_5$ is CH(OR$_{12}$)$_2$, CHO and HC=NOR$_{11}$ may be prepared as shown below in Flow Diagram XIII.

FLOW DIAGRAM XIII

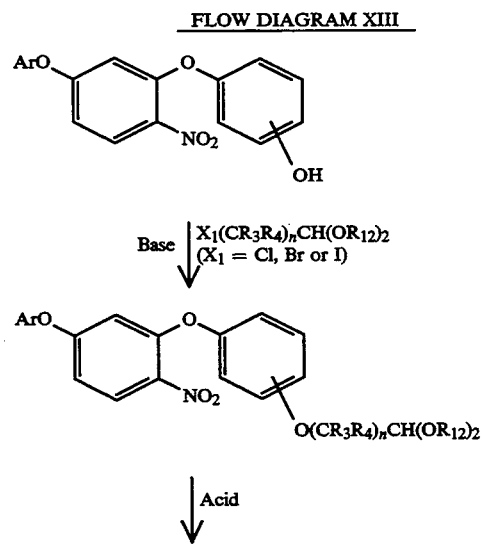

-continued
FLOW DIAGRAM XIII

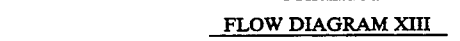

↓ H$_2$NOR$_{11}$

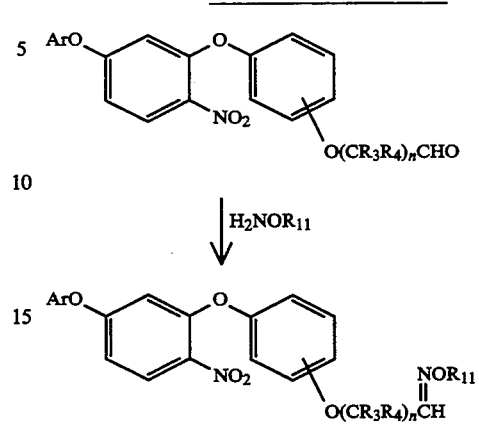

Advantageously, compounds of formula I wherein R$_5$ is cyano, and n is an integer of 1, 2, 3, 4 or 5 may be prepared as shown below in Flow Diagram XIV.

FLOW DIAGRAM XIV

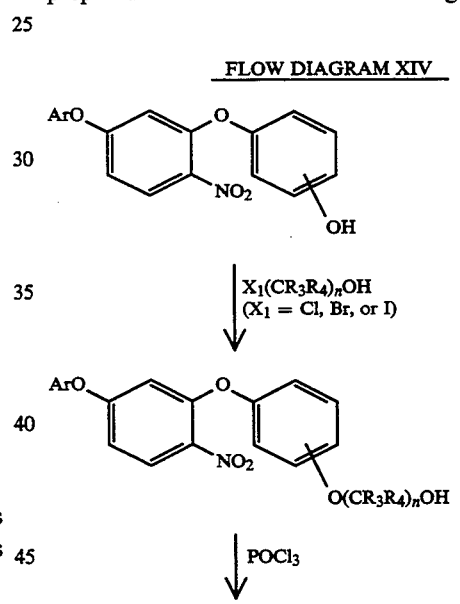

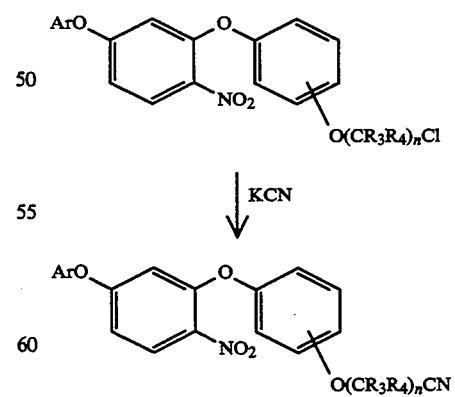

Certain aryloxybenzene compounds wherein R$_{10}$ is C$_1$-C$_4$alkyl optionally substituted with C$_1$-C$_4$alkoxy, and n is an integer of 1, 2, 3, 4 or 5 may be prepared as shown below in Flow Diagram XV.

FLOW DIAGRAM XV

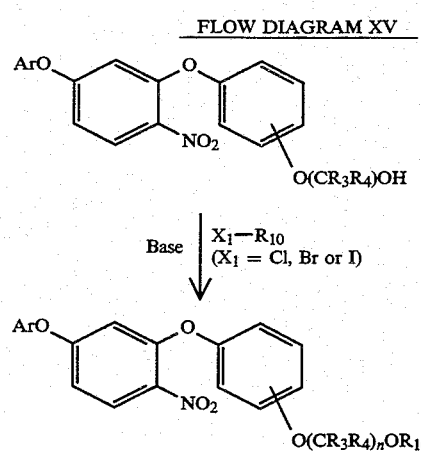

Similarly, certain compounds of formula I wherein $R_{11}$ is $C_1$–$C_4$alkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, and n is an integer of 1, 2, 3, 4 or 5 may be prepared as shown below in Flow Diagram XVI.

FLOW DIAGRAM XVI

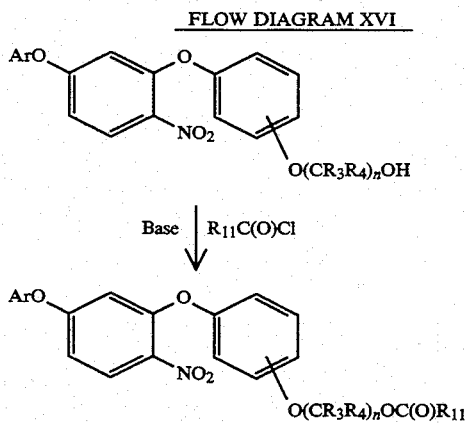

Certain aryloxybenzene compounds wherein $R_5$ is $C_2$–$C_6$alkenyl substituted with one $CO_2R_{11}$ group may be prepared as shown below in Flow Diagram XVII.

FLOW DIAGRAM XVII

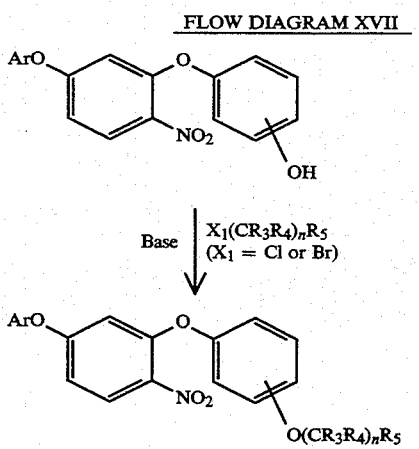

Other compounds of formula I wherein $R_9$ is OH may be prepared as shown below in Flow Diagram XVIII.

FLOW DIAGRAM XVIII

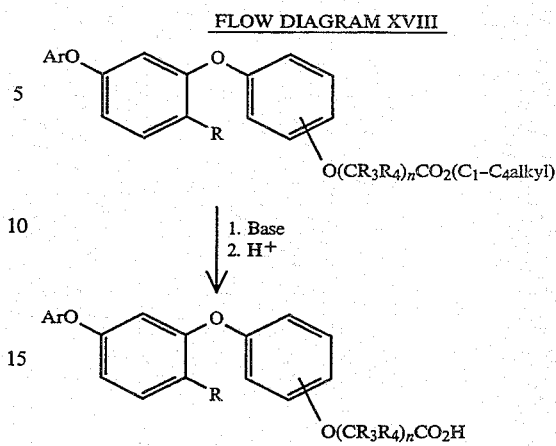

Advantageously, formula I compounds wherein $R_{14}$ is an alkali metal, alkaline earth metal, manganese, copper, zinc, cobalt, silver, nickel, ammonium or organic ammonium cation may be prepared from formula I compounds wherein $R_9$ is OH by conventional processes known to those skilled in the art.

The formula I aryloxybenzene compounds of the present invention are effective herbicidal agents useful for the control of a wide variety of undesirable plant species. Those compounds are effective for controlling weeds native to both dry land and wet land areas. The compounds are also useful as aquatic herbicides and are effective in controlling the above-said plants when applied to the foliage thereof or to soil or water containing seeds or other propagating organs thereof such as stolons, tubers or rhizomes, at rates of from about 0.016 to 4.0 kg/ha and preferably from about 0.125 to 4.0 kg/ha.

Advantageously, it has been found that the compounds of the present invention are effective for controlling undesirable plant species including important weeds in transplanted rice culture. The compounds may be applied to the soil or water containing transplanted rice plants and seeds or other propagating organs of a variety of weed species.

The compounds of this invention are best suited for use as broad spectrum herbicides, especially when applied postemergence to the locus in which weed control is desired. However, certain compounds of this invention are selective. In fact, some of the compounds of this invention are selective in crops such as soybeans, corn and rice.

While the compounds of this invention are effective for controlling undesirable plant species when employed alone, they may also be used in combination with other biological chemicals, including other herbicides.

The formula I compounds of this invention may be applied to crops in the form of a solid or liquid herbicidal composition, comprising a herbicidally effective amount of the formula I compound dispersed or dissolved in an inert solid or liquid carrier. The formulations may be applied as preemergence or post-emergence treatments.

Advantageously, the formula I compounds can be formulated as emulsifiable concentrates, wettable powders, granular formulations, flowable concentrates and the like.

In order to facilitate a further understanding of the invention, the following examples are presented primarily for the purpose of illustrating more specific details thereof. The examples generally utilize the above reaction schemes and also provide further means for preparing even more compounds of the present invention which are not specifically described above. The invention should not be deemed limited by the examples as the full scope of the invention is defined in the claims. The term NMR designates nuclear magnetic resonance spectroscopy.

EXAMPLE 1

Preparation of Methyl 2-{p-{5-[(2 -chloro-α,α,α,6-tetrafluoro-p-tolyl)oxy]-2-nitrophenoxy}phenoxy}propionate

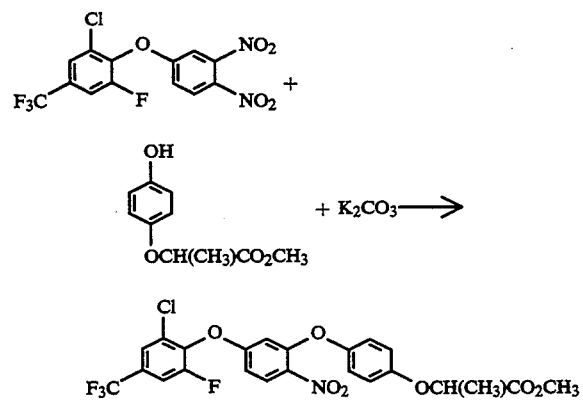

A mixture of 2-chloro-α,α,α,6-tetrafluoro-p-tolyl 3,4-dinitrophenyl ether (5.0 g, 0.013 mol), methyl 2-(p-hydroxyphenoxy)propionate (5.15 g, 0.026 mol) and potassium carbonate (3.6 g, 0.026 mol) in acetonitrile is refluxed for 18 hours, cooled to room temperature, poured into water and extracted with ether. The organic extract is washed with brine, dried over anhydrous sodium sulfate and concentrated in vacuo to obtain a residue. Column chromatography of the residue using silica gel and methylene chloride gives an oil. A solution of the oil in ether is washed sequentially with saturated sodium hydrogen carbonate solution and water, dried over anhydrous sodium sulfate and concentrated in vacuo to obtain the title product as a yellow oil (1.6 g) which is identified by $^1$HNMR and $^{13}$CNMR spectral analyses.

Using essentially the same procedure, but using the appropriately substituted ether and phenol, the following compounds are obtained:

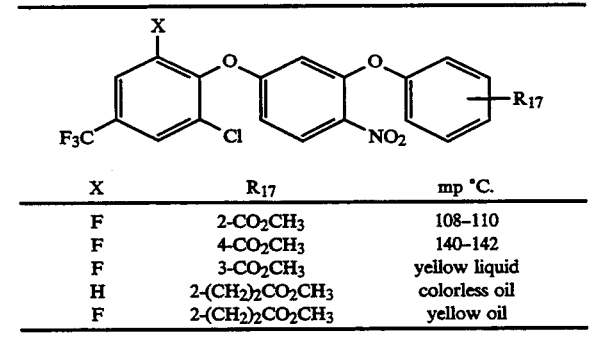

| X | R$_{17}$ | mp °C. |
|---|---|---|
| F | 2-CO$_2$CH$_3$ | 108–110 |
| F | 4-CO$_2$CH$_3$ | 140–142 |
| F | 3-CO$_2$CH$_3$ | yellow liquid |
| H | 2-(CH$_2$)$_2$CO$_2$CH$_3$ | colorless oil |
| F | 2-(CH$_2$)$_2$CO$_2$CH$_3$ | yellow oil |

EXAMPLE 2

Preparation of 4-[(2-Chloro-α,α,α,6-tetrafluoro-p-tolyl)oxy]-2-(p-methoxyphenoxy)-1-nitrobenzene

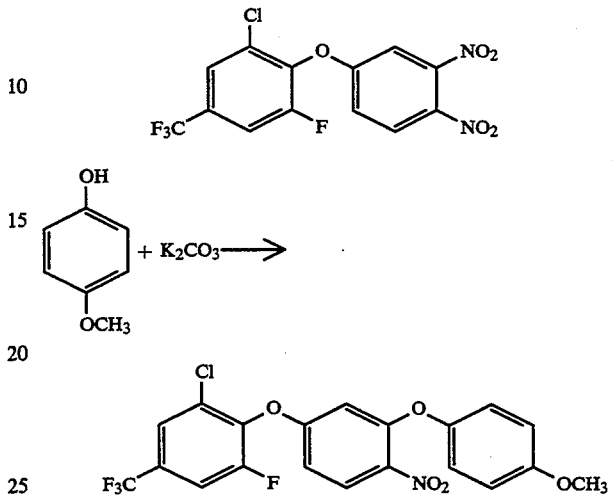

A mixture of 2-chloro-α,α,α,6-tetrafluoro-p-tolyl 3,4-dinitrophenyl ether (10.0 g, 0.026 mol), 4methoxyphenol (6.45 g, 0.052 mol) and potassium carbonate (7.26 g, 0.052 mol) in acetonitrile is refluxed for 18 hours, cooled to room temperature, poured into water and extracted with ethyl acetate. The organic extract is washed with brine, dried over anhydrous sodium sulfate and concentrated in vacuo to obtain an amber oil. Column chromatography of the oil using silica gel and a (1:4) ether/hexanes solution gives the title product as a yellow oil (3.0 g) which is identified by $^1$HNMR and $^{13}$CNMR spectral analyses.

Using essentially the same procedure, but using the appropriately substituted ether and phenol, the following compounds are obtained:

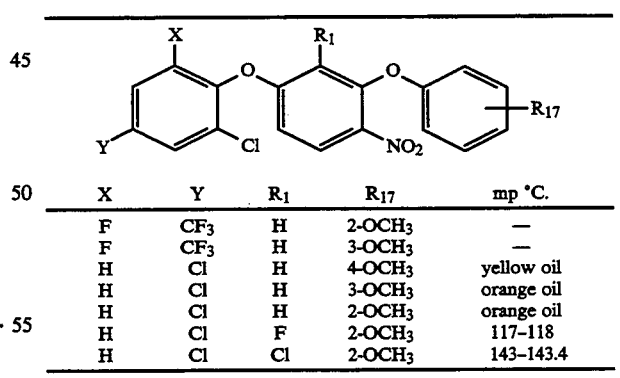

| X | Y | R$_1$ | R$_{17}$ | mp °C. |
|---|---|---|---|---|
| F | CF$_3$ | H | 2-OCH$_3$ | — |
| F | CF$_3$ | H | 3-OCH$_3$ | — |
| H | Cl | H | 4-OCH$_3$ | yellow oil |
| H | Cl | H | 3-OCH$_3$ | orange oil |
| H | Cl | H | 2-OCH$_3$ | orange oil |
| H | Cl | F | 2-OCH$_3$ | 117–118 |
| H | Cl | Cl | 2-OCH$_3$ | 143–143.4 |

EXAMPLE 3

Preparation of p-{5-[(2-Chloro-α,α,α,6-tetrafluoro-p-tolyl)oxy]-2-nitrophenoxy}phenol

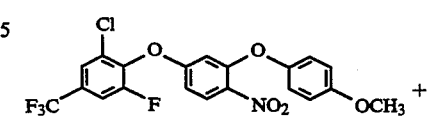

-continued

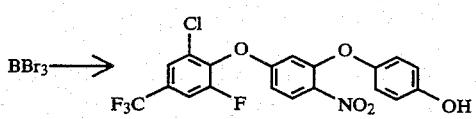

A solution of 4-[(2-chloro-α,α,α,6-tetrafluoro-p-tolyl)oxy]-2-(p-methoxyphenoxy)-1-nitrobenzene (12.4 g, 0.027 mol) in methylene chloride is cooled to −78° C., treated with boron tribromide (68 mL of a 1M solution in methylene chloride, 0.068 mol), stirred at −78° C. for two hours, warmed to room temperature and poured onto cracked ice. After the ice has melted, the phases are separated and the aqueous phase is extracted with methylene chloride. The organic phase is combined with the organic extracts and the resultant organic solution is washed with brine and dried over anhydrous sodium sulfate. Silica gel (5 g) is added to the dried organic solution and the mixture is concentrated in vacuo to obtain a brown powder. The powder is placed on top of silica gel in a flash chromatography column and eluted with a (1:1) ether/hexanes solution to give the title product as a brown oil (7.5 g) which is identified by $^1$HNMR and $^{13}$CNMR spectral analyses.

Using essentially the same procedure, but substituting the appropriately substituted nitrobenzene for 4-[(2-chloro-α,α,α,6-tetrafluoro-p-tolyl)oxy]-2-(p-methoxyphenoxy)-1-nitrobenzene, the following compounds are obtained:

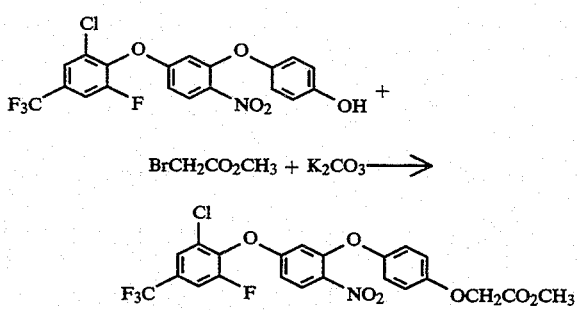

| X | Y | $R_1$ | $R_{17}$ | mp °C. |
|---|---|---|---|---|
| F | $CF_3$ | H | 2-OH | — |
| F | $CF_3$ | H | 3-OH | — |
| H | Cl | H | 4-OH | 136–138 |
| H | Cl | H | 3-OH | 145.4–145.9 |
| H | Cl | H | 2-OH | 102.7–103.7 |
| H | Cl | F | 2-OH | 180–181 |
| H | Cl | Cl | 2-OH | 103–130.5 |

EXAMPLE 4

Preparation of Methyl }p-}5-[(2-Chloro-α,α,α,6-tetrafluoro-p-tolyl)oxy]-2-nitrophenoxy}phenoxy}acetate

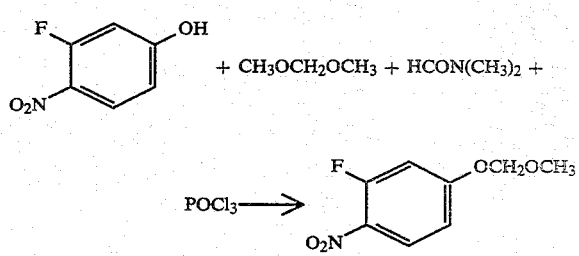

A mixture of p-{5-[(2-chloro-α,α,α,6-tetrafluoro-p-tolyl)oxy]-2-nitrophenoxy}phenol (2.0 g, 4.5 mmol), methyl bromoacetate (1.38 g, 9.0 mmol) and potassium carbonate (1.24 g, 9.0 mmol) in N,N-dimethylformamide is stirred at room temperature for three days, poured into water and extracted with ether. The organic extract is washed with brine, dried over anhydrous sodium sulfate and concentrated in vacuo to obtain a yellow oil. Column chromatography of the oil using silica gel and a 30% ether in hexanes solution gives the title product as a yellow oil (1.0 g) which is identified by $^1$HNMR and $^{13}$CNMR spectral analyses.

Using essentially the same procedure, and employing the appropriately substituted phenol and alkylating agent, the following compounds are obtained:

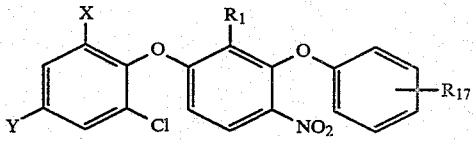

| X | Y | $R_1$ | $R_{17}$ | state |
|---|---|---|---|---|
| F | $CF_3$ | H | 3-OCH($CH_3$)$CO_2CH_3$ | yellow oil |
| H | Cl | H | 4-O($CH_2$)$_4CO_2CH_3$ | yellow oil |
| F | $CF_3$ | H | 2-OCH($CH_3$)$CO_2CH_3$ | yellow oil |
| F | $CF_3$ | H | 3-OCH$_2$CO$_2$CH$_3$ | colorless oil |
| F | $CF_3$ | H | 2-OCH$_2$CO$_2$CH$_3$ | yellow oil |
| F | $CF_3$ | H | 2-O($CH_2$)$_3CO_2CH_3$ | yellow oil |
| H | Cl | H | 4-OCH$_2$CO$_2$CH$_2$CH$_3$ | yellow oil |
| H | Cl | H | 3-OCH$_2$CO$_2$(CH$_2$)$_2$CH$_3$ | yellow oil |
| H | Cl | H | 2-OCH$_2$CO$_2$CH$_2$CH$_3$ | yellow oil |
| H | Cl | H | 3-OCH$_2$CO$_2$CH$_2$CH$_3$ | orange oil |
| H | Cl | H | 2-OCH$_2$CO$_2$(CH$_2$)$_2$CH$_3$ | yellow oil |
| H | Cl | H | 3-OCH$_2$CO$_2$CH$_3$ | orange oil |
| H | Cl | H | 4-OCH$_2$CO$_2$(CH$_2$)$_2$CH$_3$ | yellow oil |
| H | Cl | F | 2-OCH$_2$CO$_2$CH$_3$ | yellow oil |
| H | Cl | Cl | 2-OCH$_2$CO$_2$CH$_3$ | mp 139°–139.7° C. |

EXAMPLE 5

Preparation of 2-Fluoro-4-(methoxymethoxy)-1-nitrobenzene

A solution of 3-fluoro-4-nitrophenol (10.0 g, 0.064 mol), dimethoxymethane (19.3 g, 0.255 mol) and N,N-dimethylformamide (6.0 g, 0.083 mol) in toluene is heated to 65° C., treated dropwise with phosphorus oxychloride (15.7 g, 0.102 mol), stirred at 90° C. for two hours, cooled to room temperature and poured into ice water which contains five mL of 50% sodium hydroxide solution. After the ice has melted, the mixture is extracted with ether. The organic extract is washed with brine, dried over anhydrous sodium sulfate and concentrated in vacuo to give the title product as a yellow liquid (4.0 g) which is identified by $^1$HNMR spectral analysis.

EXAMPLE 6

Preparation of Methyl {o-[5-(methoxymethoxy)-2-nitrophenoxy]phenoxy}acetate

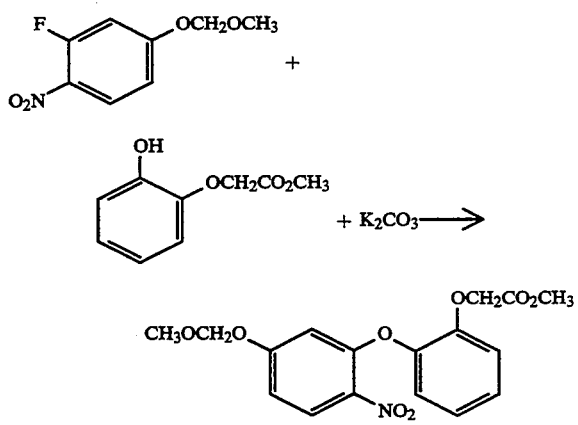

A mixture of 2-fluoro-4-(methoxymethoxy)-1-nitrobenzene (9.25 g, 0.046 mol), methyl (o-hydroxyphenoxy)acetate (8.5 g, 0.047 mol) and potassium carbonate (6.44 g, 0.047 mol) in N,N-dimethylformamide is stirred at 100° C. for 18 hours, cooled to room temperature, poured into water and extracted with ether. The organic extract is washed with brine, dried over anhydrous sodium sulfate and concentrated in vacuo to obtain an orange gum. Flash chromatography of the gum using silica gel and a 35% ethyl acetate in hexanes solution gives the title product as a yellow oil (3.6 g) which is identified by $^1$HNMR and $^{13}$CNMR spectral analyses.

Using essentially the same procedure, but substituting methyl (p-hydroxyphenoxy)acetate for methyl (o-hydroxyphenoxy)acetate, methyl {p-[5-(methoxymethoxy)-2-nitrophenoxy]phenoxy}acetate is obtained.

EXAMPLE 7

Preparation of Methyl [o-(5-hydroxy-2-nitrophenoxy)phenoxy]acetate

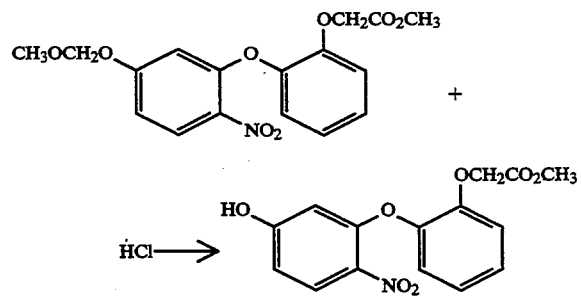

2.5N Hydrochloric acid (30 mL) is added to a solution of methyl {o-[5-(methoxymethoxy)-2-nitrophenoxy]phenoxy}acetate (3.35 g, 9.2 mmol) in methanol. The reaction mixture is refluxed for one hour, cooled to room temperature and concentrated in vacuo to give a residue. A solution of the residue in methylene chloride is washed with brine, dried over anhydrous sodium sulfate and concentrated in vacuo to obtain the title product as a yellow liquid (1.9 g) which is identified by $^1$HNMR and $^{13}$CNMR spectral analyses.

Using essentially the same procedure, but subtituting methyl {p-[5-(methoxymethoxy)-2-nitrophenoxy]phenoxy}acetate for methyl {o-[5-(methoxymethoxy)-2-nitrophenoxy]phenoxy}acetate, methyl [p-(5-hydroxy-2-nitrophenoxy)phenoxy]acetate is obtained.

EXAMPLE 8

Preparation of Methyl {o-{5-{[3-chloro-5-(trifluoromethyl)-2-pyridyl]oxy}-2-nitrophenoxy}phenoxy}acetate

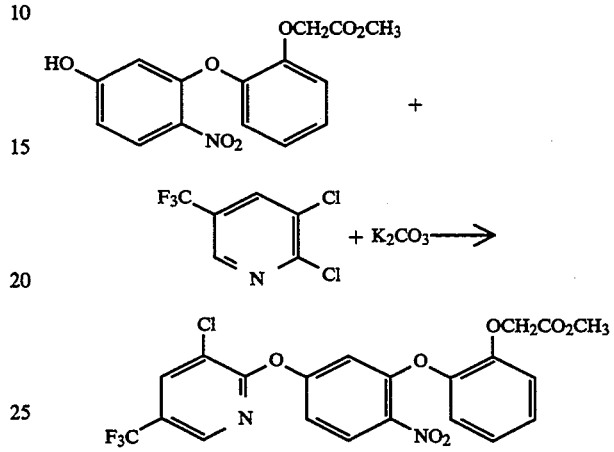

A mixture of methyl [o-(5-hydroxy-2-nitrophenoxy)phenoxy]acetate (1.9 g, 5.9 mmol), 2,3-di-chloro-5-(trifluoromethyl)pyridine (1.92 g, 8.9 mmol) and potassium carbonate (1.23 g, 8.9 mmol) in N,N-di-methylformamide is heated at 100° C. for 12 hours, cooled to room temperature, poured into water and extracted with ether. The organic extract is washed with brine, dried over anhydrous sodium sulfate and concentrated in vacuo to obtain a yellow oil. Flash chromatography of the oil using silica gel and a (1:4) ethyl acetate/hexanes solution gives the title product as a yellow liquid (0.8 g) which is identified by $^1$HNMR and $^{13}$CNMR spectral analyses.

Using essentially the same procedure, but substituting methyl [p-(5-hydroxy-2-nitrophenoxy)phenoxy]acetate for methyl [o-(5-hydroxy-2-nitrophenoxy)phenoxy]acetate, methyl {p-{5-{[3-chloro-5-(trifluoromethyl)-2-pyridyl]oxy}-2-nitrophenoxy}phenoxy}acetate is obtained.

EXAMPLE 9

Preparation of 2-Chloro-α,α,α-trifluoro-p-tolyl m-fluorophenyl ether

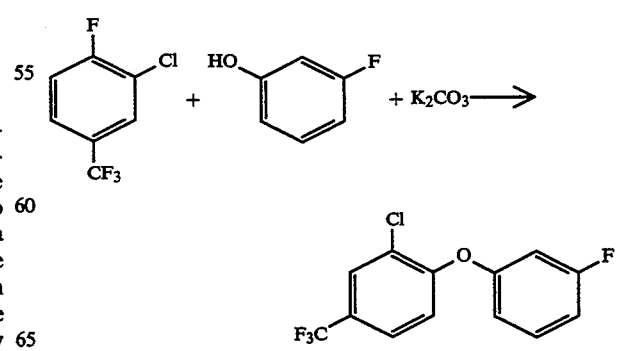

A mixture of 3-chloro-α,α,α,4-tetrafluorotoluene (30.0 g, 0.15 mol), 3-fluorophenol (20.18 g, 0.18 mol)

and potassium carbonate (24.87 g, 0.18 mol) in N,N-dimethylformamide is stirred at 100° C. for eight hours, cooled to room temperature, poured into water and extracted with ether. The organic extract is washed with brine, dried over anhydrous sodium sulfate and concentrated in vacuo to obtain the title product as an amber liquid (32.6 g) which is identified by $^1$HNMR and $^{13}$CNMR spectral analyses.

EXAMPLE 10

Preparation of 2-Chloro-α,α,α,6-tetrafluoro-p-tolyl-3-fluoro-4-nitrophenyl ether and 2-chloro-α,α,α,6-tetrafluoro-p-tolyl 3-fluoro-6-nitrophenyl ether

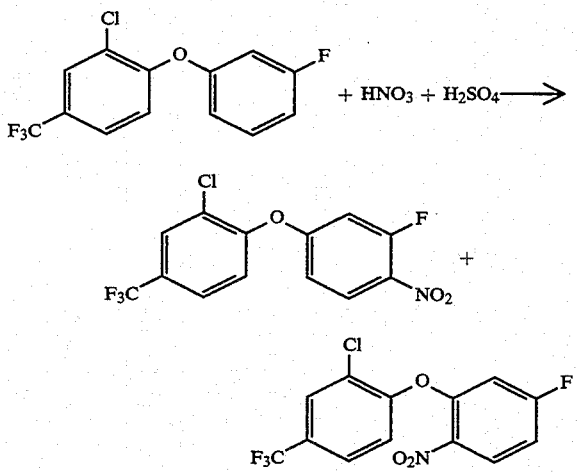

A solution of nitric acid (6.4 g of a 70% solution, 0.069 mol) in sulfuric acid (5.0 g, 0.051 mol) is added to a solution of 2-chloro-α,α,α,6-tetrafluoro-p-tolyl 3-fluoro ether (20.0 g, 0.069 mol) in acetic anhydride at −60° C. The reaction mixture is cooled to −78° C., stirred for 30 minutes, warmed to room temperature and poured onto cracked ice. After the ice has melted, the precipitate is collected, slurried in hexanes and filtered to obtain a solid. The solid is recrystallized from a hexanes/methylene chloride solution to give 2-chloro-α,α,α,6-tetrafluoro-p-tolyl carbonate solution and concentrated in vacuo to obtain an amber oil. Column chromatography of the oil using silica gel and a 10% ether in hexanes solution gives 2-chloro-α,α,α,6-tetrafluoro-p-tolyl 3-fluoro-4-nitrophenyl ether as a colorless oil (3.4 g) which is identified by $^1$HNMR and $^{13}$CNMR spectral analyses.

EXAMPLE 11

Preparation of Methyl {o-{5-[(2-chloro-α,α,α-trifluoro-p-tolyl)oxy]-2-nitrophenoxy}phenoxy}acetate

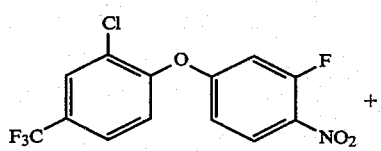

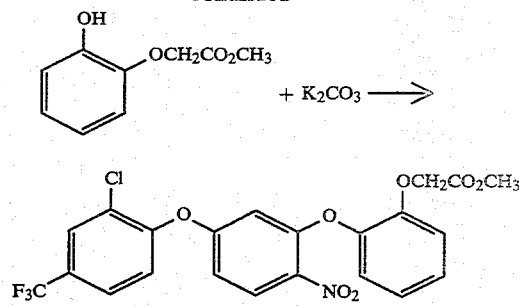

A mixture of 2-chloro-α,α,α-trifluoro-p-tolyl 3-fluoro-4-nitrophenyl ether (1.0 g, 3.0 mmol), methyl (o-hydroxyphenoxy)acetate (0.81 g, 4.5 mmol) and potassium carbonate (0.62 g, 4.5 mmol) in N,N-dimethylformamide is heated at 50° C. for 18 hours, cooled to room temperature, poured into water and extracted with ether. The organic extract is washed with brine, dried over anhydrous sodium sulfate and concentrated in vacuo to obtain a white oil. Column chromatography of the oil using silica gel and a 15% ethyl acetate in hexanes solution gives the title product as a clear liquid (0.3 g) which is identified by $^1$HNMR and $^{13}$CNMR spectral analyses.

Using essentially the same procedure, but substituting 2-chloro-α,α,α-trifluoro-p-tolyl 3-fluoro-6-nitrophenyl ether for 2-chloro-α,α,α-trifluoro-p-tolyl 3-fluoro-4-nitrophenyl ether, methyl {o-{5-[(2-chloro-α,α,α-trifluoro-p-tolyl)oxy]-4-nitrophenoxy}phenoxy}acetate is obtained.

EXAMPLE 12

Preparation of Methyl ]o-(5-fluoro-2-nitrophenoxy)phenoxy]acetate

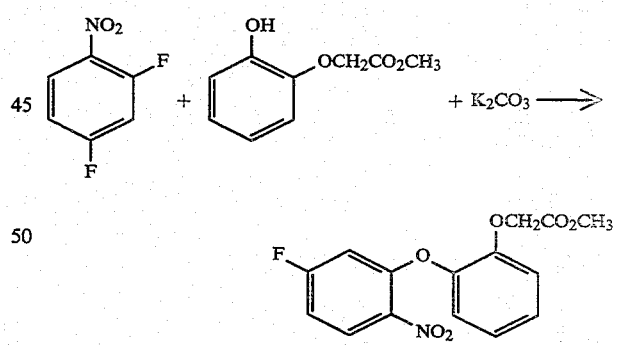

A mixture of 2,4-difluoronitrobenzene (5.0 g, 0.031 mol), methyl (o-hydroxyphenoxy)acetate (5.72 g, 0.031 mol) and potassium carbonate (4.28 g, 0.031 mol) in N,N-dimethylformamide is stirred at 100° C. for 18 hours, cooled to 25° C., poured into water and extracted with ether. The organic extract is washed with brine, dried over anyhydrous sodium sulfate and concentrated in vacuo to obtain a yellow oil. Column chromatography of the oil using silica gel and a 20% ethyl acetate in hexanes solution gives the title product as a yellow oil (1.2 g) which is identified by $^1$HNMR and $^{13}$CNMR spectral analyses.

EXAMPLE 13

Preparation of Methyl
{o-{5-{[1-methyl-5-(trifluoromethyl)pyrazol-3-yl]oxy}-2-nitrophenoxy}phenoxy}acetate

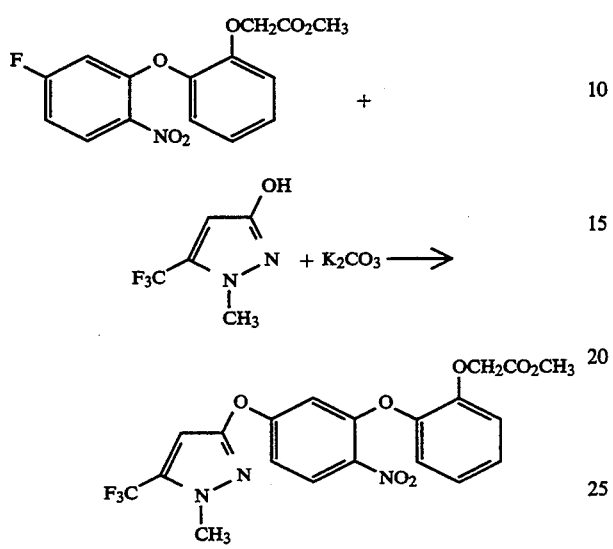

A mixture of methyl [o-(5-fluoro-2-nitrophenoxy)-phenoxy]acetate (1.1 g, 3.4 mmol), 1-methyl-5-(trifluoromethyl)pyrazol-3-ol (0.63 g, 3.8 mmol) and potassium carbonate (0.53 g, 3.8 mmol) in N,N-dimethylformamide is stirred at 100° C. for 18 hours, cooled to room temperature, poured into water and extracted with ethyl acetate. The organic extract is washed with brine, dried over anhydrous sodium sulfate and concentrated in vacuo to obtain an orange oil. Column chromatography of the oil using silica gel and a 30% ethyl acetate in hexanes solution gives the title product as a yellow oil (0.5 g) which is identified by $^1$HNMR and $^{13}$CNMR spectral analyses.

Using essentially the same procedure, but substituting the appropriately substituted pyrazol-3-ol or phenol for 1-methyl-5-(trifluoromethyl)pyrazol-3-ol, the following compounds are obtained:

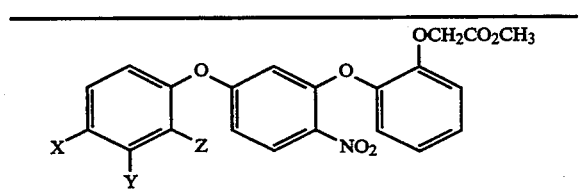

| X | Y | Z | mp °C. |
|---|---|---|---|
| F | H | Cl | 74 |
| OCF$_3$ | H | H | brown oil |
| Cl | CH$_3$ | Cl | amber oil |

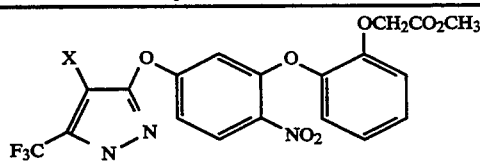

| X | state |
|---|---|
| Cl | yellow oil |

EXAMPLE 14

Preparation of Methyl
{p-{5-[(2-chloro-α,α,α,6-tetrafluoro-p-tolyl)oxy]-2-nitroanilino}phenoxy}acetate

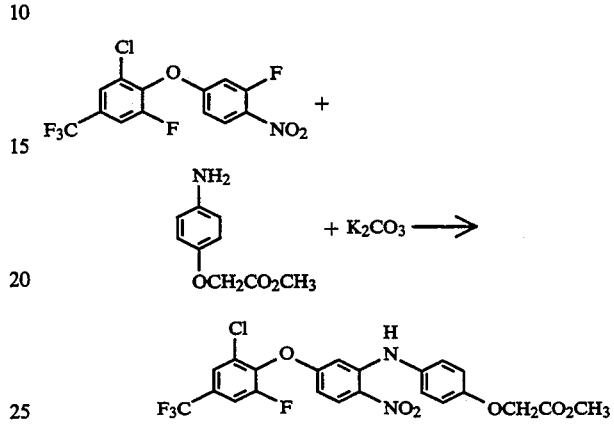

A mixture of 2-chloro-α,α,α,6-tetrafluoro-p-tolyl 3-fluoro-4-nitrophenyl ether (2.1 g, 0.006 mol), methyl (p-aminophenoxy)acetate (2.7 g, 0.015 mol) and potassium carbonate (2.0 g, 0,015 mol) in N,N-dimethyl formamide is stirred at 80° C. for 18 hours, cooled to room temperature, poured into brine and extracted with ethyl acetate. The organic extract is washed with brine, dried over anhydrous sodium sulfate and concentrated in vacuo to obtain a residue. Flash chromatography of the residue using silica gel and a 20% ethyl acetate in hexanes solution gives the title product as a red oil (0.6 g) which is identified by $^1$HNMR and $^{13}$CNMR spectral analyses.

EXAMPLE 15

Preparation of o-(5-Fluoro-2-nitrophenoxy)phenol

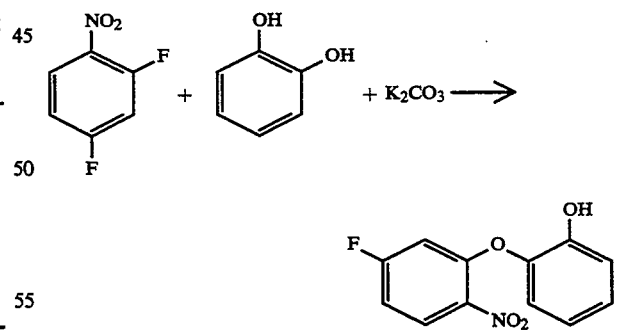

Catechol (103.8 g, 0.94 mol) and potassium carbonate (129.9 g, 0.94 mol) are added to a solution of 2,4-difluoronitrobenzene (50.0 g, 0.314 mol) in acetonitrile. The reaction mixture is stirred at 28° C. for 24 hours, poured into brine and extracted with ether. The organic extract is washed with brine, dried over anhydrous sodium sulfate and concentrated in vacuo to obtain a brown gum. Flash chromatography of the gum using silica gel and a 10% hexanes in methylene chloride solution gives the title product as a yellow solid (43 g) which is identified by $^1$HNMR spectral analysis.

EXAMPLE 16

Preparation of Methyl [o-(5-fluoro-2-nitrophenoxy]phenoxy]acetate

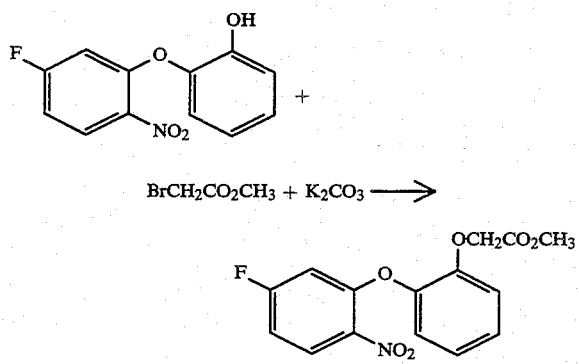

Methyl bromoacetate (36.33 g, 0.24 mol) is added to a mixture of o-(5-fluoro-2-nitrophenoxy)phenol (39.45 g, 0.16 mol) and potassium carbonate (32.75 g, 0.24 mol) in N,N-dimethylformamide. The reaction mixture is stirred at room temperature for 18 hours, poured into water and extracted with ether. The organic extract is washed with brine, dried over anhydrous sodium sulfate and concentrated in vacuo to obtain the title product as a yellow solid (42 g) which is identified by $^1$HNMR spectral analysis.

EXAMPLE 17

Preparation of Methyl {o-{5-[(2-chloro-α,α,α-trifluoro-p-tolyl)oxy]-2-nitrophenoxy}phenoxy}acetate

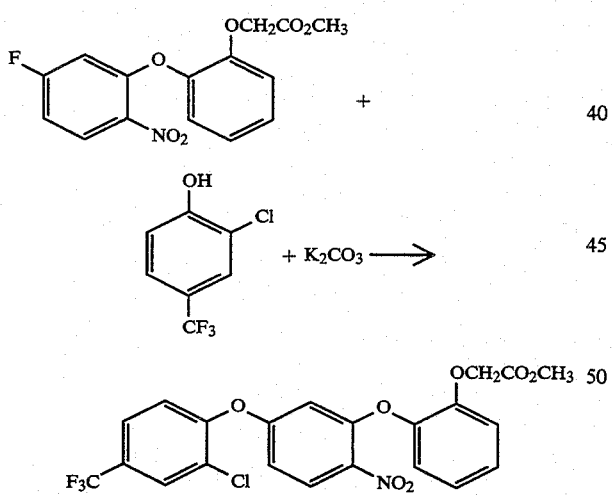

3-Chloro-4-hydroxybenzotrifluoride (50.77 g, 0.26 mol) is added to a mixture of methyl [o-(5-fluoro-2-nitrophenoxy)phenoxy]acetate (75.0 g, 0.23 mol) and potassium carbonate (35.52 g, 0.26 mol) in N,N-dimethylformamide. The reaction mixture is stirred at 80° C. for two days, cooled to room temperature, poured into water and extracted with ether. The organic extract is washed sequentially with 0.1N sodium hydroxide solution and brine and dried over anhydrous sodium sulfate. A slurry of the dried organic extract and silica gel is concentrated in vacuo to obtain a yellow solid. The solid is placed on top of silica gel in a chromatography column and eluted with a 18% ethyl acetate in hexanes solution to give the title product as a yellow oil (58 g) which is identified by $^1$HNMR and $^{13}$CNMR spectral analyses.

Using essentially the same procedure, but substituting the appropriate phenol for 3-chloro-4-hydroxybenzotrifluoride, the following compounds are obtained:

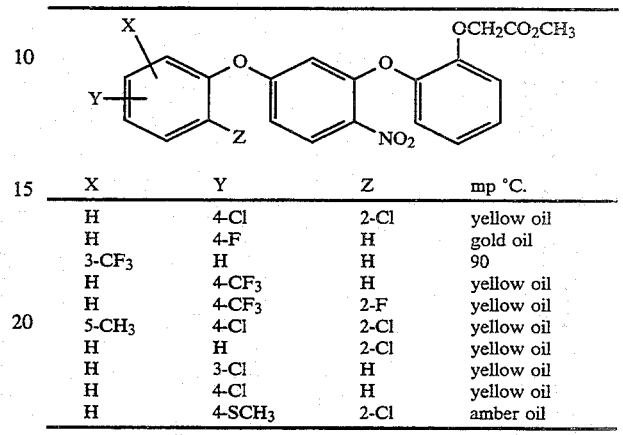

| X | Y | Z | mp °C. |
|---|---|---|---|
| H | 4-Cl | 2-Cl | yellow oil |
| H | 4-F | H | gold oil |
| 3-CF$_3$ | H | H | 90 |
| H | 4-CF$_3$ | H | yellow oil |
| H | 4-CF$_3$ | 2-F | yellow oil |
| 5-CH$_3$ | 4-Cl | 2-Cl | yellow oil |
| H | H | 2-Cl | yellow oil |
| H | 3-Cl | H | yellow oil |
| H | 4-Cl | H | yellow oil |
| H | 4-SCH$_3$ | 2-Cl | amber oil |

EXAMPLE 18

Preparation of {o-{5-[(2-Chloro-α,α,α,6-tetrafluoro-p-tolyl)oxy]-2-nitrophenoxy}phenoxy}acetic acid

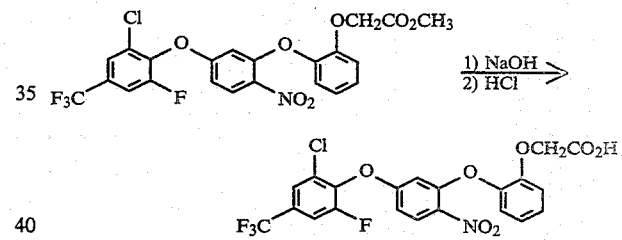

Sodium hydroxide solution (10 mL of a one normal solution, 0.01 mol) is added to a solution of methyl {o-{5-[(2-chloro-α,α,α,6-tetrafluoro-p-tolyl)oxy]-2-nitrophenoxy}phenoxy}acetate (5.25 g, 0.01 mol) in methanol. The reaction mixture is stirred for three hours, concentrated in vacuo and dissolved in water. The aqueous solution is adjusted to pH 3 with 2.5N hydrochloric acid and extracted with methylene chloride. The organic extract is washed with water, dried over anhydrous sodium sulfate and concentrated in vacuo to obtain the title product as a white solid (2 g) which is identified by $^1$HNMR and $^{13}$CNMR spectral analyses.

Using essentially the same procedure, but using the appropriately substituted ester, the following compounds are obtained:

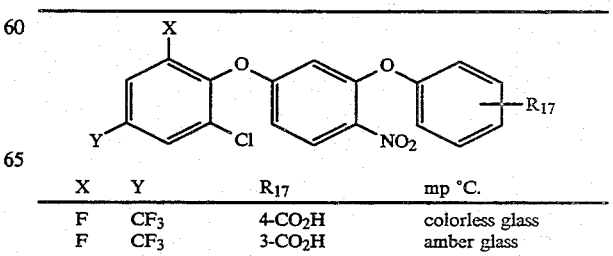

| X | Y | R$_{17}$ | mp °C. |
|---|---|---|---|
| F | CF$_3$ | 4-CO$_2$H | colorless glass |
| F | CF$_3$ | 3-CO$_2$H | amber glass |

-continued

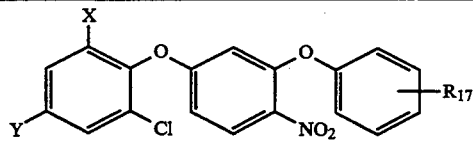

| X | Y | R₁₇ | mp °C. |
|---|---|---|---|
| H | Cl | 3-OCH₂CO₂H | off-white solid |
| H | Cl | 4-OCH₂CO₂H | 146-150 |
| H | Cl | 2-OCH₂CO₂H | yellow oil |
| H | S(O)CH₃ | 2-OCH₂CO₂H | 73-79 |

EXAMPLE 19

Preparation of
{o-[5-(2,4-Dichlorophenoxy)-2-nitrophenoxy]phenoxy}acetyl chloride

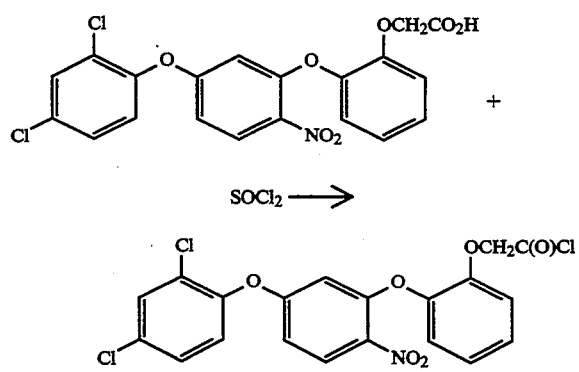

A mixture of thionyl chloride (25.0 mL, 343 mmol) and {o-[5-(2,4-dichlorophenoxy)-2-nitrophenoxy]-phenoxy}acetic acid (4.06 g, 9.02 mmol) is refluxed for one hour. Excess thionyl chloride is then removed from the reaction mixture via distillation to give the title product (4.3 g) which is identified by ¹HNMR and ¹³CNMR spectral analyses.

EXAMPLE 20

Preparation of
2-{o-[5-(2,4-Dichlorophenoxy)-2-nitrophenoxy]-phenoxy}acetamide

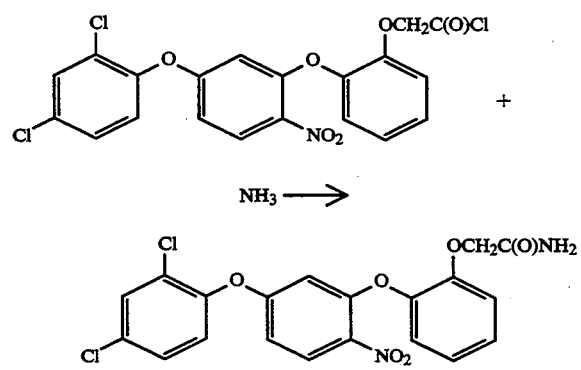

A mixture of {o-[5-(2,4-dichlorophenoxy)-2nitrophenoxy]phenoxy}acetyl chloride (1.11 g, 2.38 mmol), ammonia solution (5 mL of a 35% solution), ethanol (5 mL) and N,N-dimethylformamide (10 mL) is stirred for one hour, poured into water and extracted with an ether/ethyl acetate (1:1) solution. The combined organic extracts are washed sequentially with water and brine, dried over anhydrous magnesium sulfate and concentrated in vacuo to give the title product as a yellow oil (1.0 g) which is identified by NMR spectral analyses.

EXAMPLE 21

Preparation of
1-Diazo-3-{o-[5-(2,4-dichlorophenoxy)-2-nitrophenoxy]phenoxy}-2-propanone

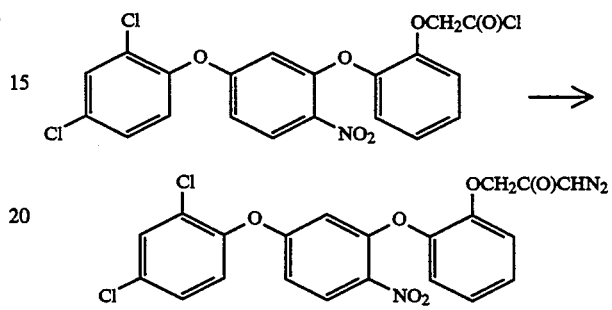

A mixture of potassium hydroxide in methanol (20.0 mL of a 4M solution) is heated to 42° C. and treated dropwise with a mixture of N-methyl-N-nitroso-p-toluenesulfonamide (4 g, 18.7 mmol) in ether (40 mL). The diazomethane is distilled over, condensed with a dry ice/acetone condenser and collected. The diazomethane/ether solution is stirred in an ice-bath, treated dropwise with a solution of {o-[5-(2,4-dichlorophenoxy)-2-nitrophenoxy]phenoxy}acetyl chloride (1.09 g, 2.32 mmol) in tetrahydrofuran, stirred for 30 minutes and concentrated in vacuo to give the title product as a yellow oil which is identified by NMR spectral analyses.

EXAMPLE 22

Preparation of Methyl
3-{o-[5-(2,4-dichlorophenoxy)-2-nitrophenoxy]phenoxy}propionate

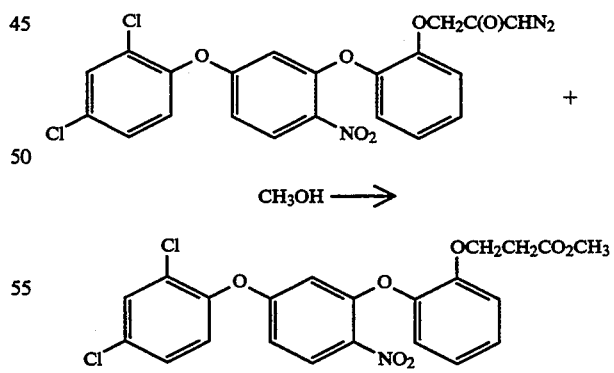

A solution of 1-diazo-3-{o-[5-(2,4-dichlorophenoxy)-2-nitrophenoxy]phenoxy}-2-propanone (1.0 g, 2.11 mmol) in methanol is irradiated with a 125 watt ultraviolet lamp for two and one-half hours under a nitrogen atmosphere. The reaction mixture is concentrated in vacuo and chromatographed using silica gel and an ethyl acetate in hexanes solution to obtain an oil. The oil is repurified by column chromatography using silica gel and a hexanes in dichloromethane solution to give the title product as a yellow oil (0.18 g) which is identified by NMR spectral analyses.

EXAMPLE 23

Preparation of Benzyl {o-[5-(2,4-dichlorophenoxy)-2-nitrophenoxy]phenoxy-}acetate

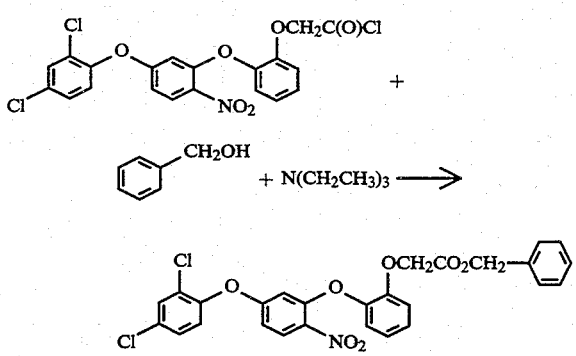

Benzyl alcohol (0.8 mL, 7.73 mmol) and triethylamine (1 mL, 7.17 mmol) are added to a mixture of {o-[5-(2,4-dichlorophenoxy)-2-nitrophenoxy]phenoxy}acetyl chloride (1.12 g, 2.38 mmol) in tetrahydrofuran. The reaction mixture is stirred for twenty minutes, poured into water and extracted with ether. The combined organic extracts are washed sequentially with one molar hydrochloric acid, water and brine, dried over anhydrous magnesium sulfate and concentrated in vacuo to obtain an oil. Column chromatography of the oil using silica gel and a hexanes in methylene chloride solution gives the title product as a yellow oil (1.0 g) which is identified by NMR spectral analyses.

EXAMPLE 24

Preparation of Methyl {o-{5-[2-chloro-4-(methylsulfinyl)phenoxy]-2-nitrophenoxy}phenoxy}acetate

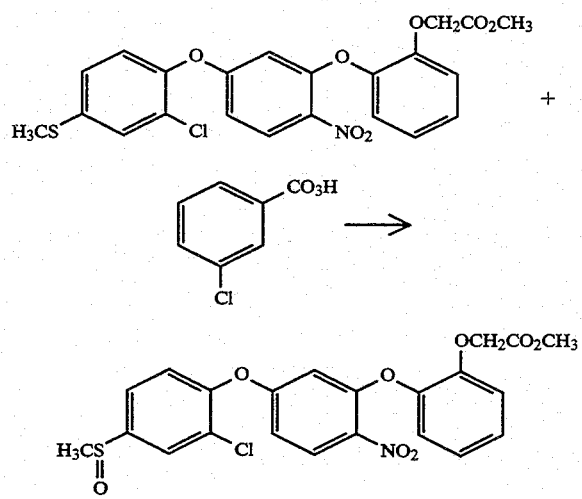

A solution of methyl {o-{5-[2-chloro-4-(methylthio)-phenoxy]-2-nitrophenoxy}phenoxy}acetate (4.30 g, 0.009 mol) in methylene chloride is cooled to 0° C. and treated with 3-chloroperoxybenzoic acid (1.73 g, 0.010 mol). The reaction mixture is warmed to room temperature, stirred overnight, quenched with triethylamine (1.4 mL) and concentrated in vacuo. The residue is dissolved into ethyl acetate and the organic solution is washed sequentially with water and 2 N hydrochloric acid, dried over anhydrous sodium sulfate and concentrated in vacuo to obtain an amber oil. Column chromatography of the oil using silica gel and ethyl acetate gives the title product as an amber oil (2.6 g) which is identified by NMR spectral analyses.

Using essentially the same procedure, but employing two molar equivalents of 3-chloroperoxybenzoic acid, methyl {o-{5-[2-chloro-4-(methylsulfonyl)phenoxy]-2-nitrophenoxy}phenoxy}acetate is obtained as a yellow glass.

EXAMPLE 25

Postemergence herbicidal evaluation of test compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantities to provide the equivalent of about 0.125 kg to 0.500 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this postemergence herbicidal evaluation and in the preemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | % Control Compared to Check |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

PLANT SPECIES EMPLOYED
IN HERBICIDAL EVALUATIONS

| Header Abb. | Common Name | Scientific Name |
|---|---|---|
| ABUTH | Velvetleaf | ABUTILON THEOPHRASTI, MEDIC. |
| AMARE | Pigweed, Redroot | AMARANTHUS RETROFLEXUS, L. |
| AMBEL | Ragweed, Common | AMBROSIA ARTEMISIIFOLIA, L. |
| IPOHE | Morningglory, Ivylea | IPOMOEA HEDERACEA, (L) JACQ. |
| DIGSA | Crabgrass, (Hairy) L | DIGITARIA SANGUINALIS, (L) SCOP |
| ECHCG | Barnyardgrass | ECHINOCHLOA CRUS-GALLI, (L) BEAU |
| PANMIY | Millet, Yellow | PANICUM MILIACEUM, L. |
| SETVI | Foxtail, Green | SETARIA VIRIDIS, (L) BEAUV |
| GLXMAW | Soybean, Williams | GLYCINE MAX (L) MERR. CV. WILLIAMS |
| ORYSA | Rice | ORYZA SATIVA L. |
| TRZAWO | Wheat, Winter, Cv. Apollo | TRITICUM AESTIVUM, CV APOLLO |
| ZEAMX | Corn, Field | ZEA MAYS, L. |

COMPOUNDS EVALUATED AS HERBICIDAL AGENTS

| Compound No. | |
|---|---|
| 1 | Methyl 2-{p-{5-[(2-chloro-α,α,α,6-tetrafluoro-p-tolyl)oxy]-2-nitrophenoxy}phenoxy}propionate |
| 2 | Methyl 2-{m-{5-[(2-chloro-α,α,α,6-tetrafluoro-p-tolyl)oxy]-2-nitrophenoxy}phenoxy}propionate |
| 3 | Methyl 2-{o-{5-[(2-chloro-α,α,α,6-tetrafluoro-p-tolyl)oxy]-2-nitrophenoxy}phenoxy}propionate |
| 4 | Methyl {m-{5-[(2-chloro-α,α,α,6-tetrafluoro-p-tolyl)oxy]-2-nitrophenoxy}phenoxy}acetate |
| 5 | Methyl {o-{5-[(2-chloro-α,α,α,6-tetrafluoro-p-tolyl)oxy]-2-nitrophenoxy}phenoxy}acetate |
| 6 | Methyl {p-{5-[(2-chloro-α,α,α,6-tetrafluoro-p-tolyl)oxy]-2-nitrophenoxy}phenoxy}acetate |
| 7 | Methyl {o-{5-{[3-chloro-5-(trifluoromethyl)-2-pyridyl]oxy}-2-nitrophenoxy}phenoxy}acetate |
| 8 | Methyl {p-{5-{[3-chloro-5-(trifluoromethyl)-2-pyridyl]oxy}-2-nitrophenoxy}phenoxy}acetate |
| 9 | {o-{5-[(2-Chloro-α,α,α,6-tetrafluoro-p-tolyl)oxy]-2-nitrophenoxy}phenoxy}acetic acid |
| 10 | Methyl {o-{5-[(2-chloro-α,α,α-trifluoro-p-tolyl)oxy]-4-nitrophenoxy}phenoxy}acetate |
| 11 | Methyl o-{5-[(2-chloro-α,α,α,6-tetrafluoro-p-tolyl)oxy]-2-nitrophenoxy}benzoate |
| 12 | Methyl {o-{5-[(2-chloro-α,α,α-trifluoro-p-tolyl)oxy]-2-nitrophenoxy}phenoxy}acetate |
| 13 | Methyl p-{5-[(2-chloro-α,α,α,6-tetrafluoro-p-tolyl)oxy]-2-nitrophenoxy}benzoate |
| 14 | Methyl m-{5-[(2-Chloro-α,α,α,6-tetrafluoro-p-tolyl)oxy]-2-nitrophenoxy}benzoate |
| 15 | p-{5-[(2-Chloro-α,α,α,6-tetrafluoro-p-tolyl)oxy]-2-nitrophenoxy}benzoic acid |
| 16 | m-{5-[(2-Chloro-α,α,α,6-tetrafluoro-p-tolyl)oxy]-2-nitrophenoxy}benzoic acid |
| 17 | Methyl o-{5-[(2-chloro-α,α,α-trifluoro-p-tolyl)oxy]-2-nitrophenoxy}hydrocinnamate |
| 18 | Methyl 4-{o-{5-[(2-chloro-α,α,α,6-tetrafluoro-p-tolyl)-oxy]-2-nitrophenoxy}phenoxy}-butyrate |
| 19 | Methyl 3-{o-{5-[(2-chloro-α,α,α,6-tetrafluoro-p-tolyl)oxy]-2-nitrophenoxy}phenoxy}propionate |
| 20 | Methyl {p-{5-[(2-chloro-α,α,α,6-tetrafluoro-p-tolyl)oxy]-2-nitroanilino}phenoxy}acetate |
| 21 | Methyl {o-{5-{[1-methyl-5-(trifluoromethyl)pyrazol-3-yl]-oxy}-2-nitrophenoxy}phenoxy}acetate |
| 22 | Methyl {o-{5-{[4-chloro-1-methyl-5-(trifluoromethyl)pyrazol-3-yl]-oxy}-2-nitrophenoxy}phenoxy}acetate |
| 23 | Methyl {o-[5-(2-chloro-4-fluorophenoxy)-2-nitrophenoxy]phenoxy}-acetate |
| 24 | Methyl {o-{5-[p-(trifluoromethoxy)phenoxy]-2-nitrophenoxy}phenoxy}acetate |
| 25 | Methyl {o-[5-(2,4-dichlorophenoxy)-2-nitrophenoxy]phenoxy}acetate |
| 26 | Methyl {o-[5-(p-fluorophenoxy)-2-nitrophenoxy]phenoxy}acetate |
| 27 | Methyl {o-{5-[(6-chloro-α,α,α-trifluoro-m-tolyl)oxy]-2-nitrophenoxy}phenoxy}acetate |
| 28 | Methyl {o-{2-nitro-5-[(α,α,α-trifluoro-p-tolyl)oxy]phenoxy}-phenoxy}acetate |
| 29 | Methyl {o-{2-nitro-5-[(α,α,α,2-tetrafluoro-p-tolyl)oxy]phenoxy} phenoxy}acetate |
| 30 | Methyl {o-{5-[(4,6-dichloro-m-tolyl)oxy]-2-nitrophenoxy}-phenoxy}acetate |
| 31 | Methyl {o-{5-[(2,4-dichloro-m-tolyl)oxy]-2-nitrophenoxy}-phenoxy}acetate |
| 32 | Methyl {m-[5-(2,4-dichlorophenoxy)-2-nitrophenoxy]-phenoxy}acetate |
| 33 | Ethyl {m-[5-(2,4-dichlorophenoxy)-2-nitrophenoxy]phenoxy}acetate |
| 34 | {m-[5-(2,4-Dichlorophenoxy)-2-nitrophenoxy]phenoxy}acetic acid |
| 35 | Ethyl {p-[5-(2,4-dichlorophenoxy)-2-nitrophenoxy]phenoxy}acetate |
| 36 | Propyl {p-[5-(2,4-dichlorophenoxy)-2-nitrophenoxy]phenoxy}acetate |
| 37 | Methyl 5-{p-[5-(2,4-dichlorophenoxy)-2-nitrophenoxy]phenoxy}-pentanoate |
| 38 | {p-[5-(2,4-Dichlorophenoxy)-2-nitrophenoxy]acetic acid |
| 39 | {o-{5-[2-Chloro-4-(methylsulfinyl)-phenoxy]-2-nitrophenoxy}phenoxy}-acetic acid |
| 40 | Methyl {o-{5-[2-chloro-4-(methylsulfinyl)phenoxy]-2-nitrophenoxy}-phenoxy}acetate |
| 41 | Methyl {o-[5-(m-chlorophenoxy)-2-nitrophenoxy]phenoxy}acetate |
| 42 | Methyl {o-[5-(p-chlorophenoxy)-2-nitrophenoxy]phenoxy}acetate |
| 43 | Methyl {o-[5-(o-chlorophenoxy)-2-nitrophenoxy]phenoxy}acetate |

TABLE 1

Postemergence Herbicidal Evaluations of Test Compounds

| Cpd. No. | Rate (kg/ha) | ABUTH | AMARE | AMBEL | IPOHE | DIGSA | ECHCG | PANMIY | SETVI |
|---|---|---|---|---|---|---|---|---|---|

TABLE 1-continued

Postemergence Herbicidal Evaluations of Test Compounds

| | | | | | | | | | |
|---|---|---|---|---|---|---|---|---|---|
| 1 | 0.500 | 8.3 | 9.0 | 9.0 | 9.0 | 1.0 | 4.0 | 4.5 | 4.7 |
| | 0.250 | 8.7 | 9.0 | 9.0 | 9.0 | 4.5 | 2.5 | 3.5 | 4.3 |
| | 0.125 | 8.3 | 9.0 | 9.0 | 9.0 | 3.0 | 2.0 | 3.0 | 3.3 |
| 2 | 0.500 | 7.0 | 9.0 | 9.0 | 9.0 | 4.0 | 2.0 | 4.0 | 5.0 |
| | 0.250 | 8.0 | 9.0 | 9.0 | 9.0 | 3.0 | 2.0 | 3.0 | 2.0 |
| | 0.125 | 6.0 | 9.0 | 9.0 | 6.0 | 3.0 | 2.0 | 2.0 | 2.0 |
| 3 | 0.500 | 8.0 | 9.0 | 8.0 | 9.0 | 7.0 | 6.0 | 4.0 | 4.0 |
| | 0.250 | 8.0 | 9.0 | 9.0 | 9.0 | 4.0 | 3.0 | 3.0 | 4.0 |
| | 0.125 | 8.0 | 9.0 | 9.0 | 9.0 | 4.0 | 3.0 | 4.0 | 4.0 |
| 4 | 0.500 | 6.0 | 9.0 | 9.0 | 9.0 | 5.0 | 2.0 | 3.0 | 3.0 |
| | 0.250 | 4.0 | 9.0 | 9.0 | 9.0 | 3.0 | 2.0 | 3.0 | 2.0 |
| | 0.125 | 3.0 | 9.0 | 7.0 | 9.0 | 3.0 | 2.0 | 3.0 | 2.0 |
| 5 | 0.500 | 9.0 | 9.0 | 9.0 | 9.0 | 8.3 | 6.7 | 6.7 | 6.8 |
| | 0.250 | 8.8 | 9.0 | 9.0 | 9.0 | 7.5 | 5.6 | 5.6 | 6.0 |
| | 0.125 | 8.9 | 9.0 | 9.0 | 9.0 | 7.0 | 5.0 | 5.1 | 5.4 |
| 6 | 0.500 | 8.0 | 9.0 | 9.0 | 9.0 | 3.0 | 3.0 | 4.0 | 3.0 |
| | 0.250 | 6.0 | 9.0 | 8.0 | 9.0 | 3.0 | 2.0 | 3.0 | 2.0 |
| | 0.125 | 7.0 | 9.0 | 8.0 | 7.0 | 3.0 | 2.0 | 3.0 | 3.0 |
| 7 | 0.500 | 9.0 | 9.0 | 9.0 | 9.0 | 9.0 | 5.0 | 6.0 | 5.0 |
| | 0.250 | 9.0 | 9.0 | 9.0 | 9.0 | 9.0 | 3.0 | 6.0 | 5.0 |
| | 0.125 | 7.0 | 9.0 | 9.0 | 9.0 | 5.0 | 2.0 | 6.0 | 4.0 |
| 8 | 0.500 | 5.0 | 8.0 | 9.0 | 9.0 | 3.0 | 2.0 | 4.0 | 2.0 |
| | 0.250 | 3.0 | 9.0 | 9.0 | 6.0 | 3.0 | 2.0 | 3.0 | 2.0 |
| | 0.125 | 3.0 | 9.0 | 9.0 | 6.0 | 3.0 | 2.0 | 2.0 | 2.0 |
| 9 | 0.125 | 9.0 | 9.0 | 9.0 | 9.0 | 8.0 | 6.0 | 4.0 | 5.0 |
| 10 | 0.125 | 8.0 | 9.0 | 6.0 | 5.0 | 1.0 | 1.0 | 1.0 | 1.0 |
| 11 | 0.125 | 7.0 | 9.0 | 7.0 | 5.0 | 1.0 | 2.0 | 3.0 | 2.0 |
| 12 | 0.125 | 9.0 | 9.0 | 9.0 | 9.0 | 8.0 | 2.5 | 4.0 | 4.0 |
| 13 | 0.125 | 9.0 | 9.0 | 9.0 | 6.0 | 1.0 | 1.0 | 2.0 | 2.0 |
| 14 | 0.125 | 9.0 | 9.0 | 8.0 | 5.0 | 2.0 | 1.0 | 2.0 | 1.0 |
| 15 | 0.125 | 9.0 | 9.0 | 9.0 | 7.0 | 2.0 | 1.0 | 2.0 | 2.0 |
| 16 | 0.125 | 9.0 | 9.0 | 7.0 | 7.0 | 2.0 | 2.0 | 2.0 | 1.0 |
| 17 | 0.125 | 9.0 | 9.0 | 7.0 | 4.0 | 0.0 | 0.0 | 1.0 | 0.0 |
| 18 | 0.500 | 9.0 | 9.0 | 6.0 | 7.0 | 6.0 | 4.0 | 3.0 | 3.0 |
| | 0.250 | 8.0 | 9.0 | 5.0 | 6.0 | 4.0 | 3.0 | 3.0 | 2.0 |
| | 0.125 | 9.0 | 9.0 | 3.0 | 5.0 | 4.0 | 3.0 | 2.0 | 2.0 |
| 19 | 0.125 | 8.0 | 9.0 | 7.0 | 6.0 | 2.0 | 1.0 | 2.0 | 1.0 |
| 20 | 0.500 | 9.0 | 9.0 | 9.0 | 9.0 | 7.0 | 4.0 | 3.0 | 3.0 |
| | 0.250 | 9.0 | 9.0 | 9.0 | 9.0 | 6.0 | 3.0 | 3.0 | 2.0 |
| | 0.125 | 9.0 | 9.0 | 9.0 | 9.0 | 6.0 | 3.0 | 2.0 | 2.0 |
| 21 | 0.500 | 9.0 | 9.0 | 9.0 | 9.0 | 9.0 | 9.0 | 6.0 | 4.0 |
| | 0.250 | 9.0 | 9.0 | 9.0 | 9.0 | 8.0 | 9.0 | 6.0 | 4.0 |
| | 0.125 | 9.0 | 9.0 | 9.0 | 9.0 | 8.0 | 9.0 | 6.0 | 4.0 |
| 22 | 0.500 | 9.0 | 9.0 | 9.0 | 9.0 | 9.0 | 8.0 | 5.0 | 5.0 |
| | 0.250 | 9.0 | 9.0 | 9.0 | 9.0 | 9.0 | 6.0 | 4.0 | 5.0 |
| | 0.125 | 9.0 | 9.0 | 9.0 | 9.0 | 6.0 | 6.0 | 4.0 | 5.0 |
| 23 | 0.500 | 9.0 | 9.0 | 9.0 | 9.0 | 9.0 | 7.0 | 7.0 | 6.0 |
| | 0.250 | 9.0 | 9.0 | 9.0 | 9.0 | 8.0 | 4.0 | 6.0 | 6.0 |
| | 0.125 | 8.0 | 9.0 | 9.0 | 9.0 | 8.0 | 4.0 | 5.0 | 6.0 |
| 24 | 0.500 | 7.0 | 9.0 | 8.0 | 9.0 | 5.0 | 3.0 | 4.0 | 5.0 |
| | 0.250 | 6.0 | 9.0 | 5.0 | 7.0 | 3.0 | 3.0 | 4.0 | 3.0 |
| | 0.125 | 4.0 | 9.0 | 5.0 | 4.0 | 2.0 | 2.0 | 3.0 | 3.0 |
| 25 | 0.500 | 9.0 | 9.0 | 9.0 | 9.0 | 6.3 | 3.8 | 4.5 | 4.5 |
| | 0.250 | 8.8 | 9.0 | 9.0 | 9.0 | 5.3 | 2.7 | 4.3 | 4.3 |
| | 0.125 | 8.5 | 9.0 | 8.8 | 8.8 | 4.3 | 2.2 | 3.5 | 3.5 |
| 26 | 0.500 | 8.0 | 9.0 | 8.0 | 9.0 | 6.0 | 5.0 | 4.0 | 4.0 |
| | 0.250 | 6.0 | 9.0 | 6.0 | 6.0 | 4.0 | 2.0 | 4.0 | 3.0 |
| | 0.125 | 6.0 | 9.0 | 6.0 | 6.0 | 4.0 | 3.0 | 4.0 | 3.0 |
| 27 | 0.500 | 3.0 | 9.0 | 6.0 | 3.0 | 3.0 | 2.0 | 2.0 | 2.0 |
| | 0.250 | 4.0 | 9.0 | 4.0 | 4.0 | 3.0 | 2.0 | 2.0 | 2.0 |
| | 0.125 | 3.0 | 8.0 | 4.0 | 3.0 | 3.0 | 2.0 | 1.0 | 2.0 |
| 28 | 0.500 | 7.0 | 9.0 | 9.0 | 9.0 | 6.0 | 5.0 | 5.0 | 5.0 |
| | 0.250 | 9.0 | 9.0 | 9.0 | 9.0 | 5.0 | 4.0 | 5.0 | 4.0 |
| | 0.125 | 5.0 | 9.0 | 8.0 | 9.0 | 5.0 | 4.0 | 4.0 | 3.0 |
| 29 | 0.500 | 8.0 | 9.0 | 9.0 | 9.0 | 7.0 | 5.0 | 5.0 | 5.0 |
| | 0.250 | 8.0 | 9.0 | 9.0 | 9.0 | 5.0 | 4.0 | 5.0 | 4.0 |
| | 0.125 | 6.0 | 9.0 | 9.0 | 9.0 | 5.0 | 4.0 | 4.0 | 4.0 |
| 30 | 0.500 | 5.0 | 9.0 | 5.0 | 6.0 | 2.0 | 3.0 | 3.0 | 3.0 |
| | 0.250 | 4.0 | 9.0 | 4.0 | 4.0 | 2.0 | 2.0 | 2.0 | 2.0 |
| | 0.125 | 3.0 | 8.0 | 3.0 | 3.0 | 2.0 | 2.0 | 2.0 | 2.0 |
| 31 | 0.500 | 8.0 | 9.0 | 9.0 | 9.0 | 6.0 | 4.0 | 5.0 | 5.0 |
| | 0.250 | 9.0 | 9.0 | 9.0 | 9.0 | 5.0 | 4.0 | 4.0 | 4.0 |
| | 0.125 | 7.0 | 9.0 | 8.0 | 9.0 | 4.0 | 4.0 | 4.0 | 3.0 |
| 32 | 0.500 | 6.0 | 9.0 | 5.0 | 8.0 | 1.0 | 2.0 | 2.0 | 1.0 |
| | 0.250 | 5.0 | 9.0 | 4.0 | 8.0 | 1.0 | 2.0 | 2.0 | 1.0 |
| | 0.125 | 4.0 | 9.0 | 3.0 | 5.0 | 1.0 | 1.0 | 2.0 | 1.0 |
| 33 | 0.500 | 3.0 | 9.0 | 2.0 | 9.0 | 1.0 | 1.0 | 1.0 | 0.0 |
| | 0.250 | 3.0 | 9.0 | 2.0 | 9.0 | 0.0 | 1.0 | 2.0 | 0.0 |
| | 0.125 | 3.0 | 7.0 | 2.0 | 5.0 | 1.0 | 1.0 | 1.0 | 0.0 |
| 34 | 0.500 | 2.0 | 9.0 | 4.0 | 9.0 | 1.0 | 1.0 | 2.0 | 1.0 |
| | 0.250 | 2.0 | 9.0 | 4.0 | 7.0 | 1.0 | 1.0 | 2.0 | 0.0 |

TABLE 1-continued
Postemergence Herbicidal Evaluations of Test Compounds

| | | | | | | | | | |
|---|---|---|---|---|---|---|---|---|---|
| | 0.125 | 2.0 | 7.0 | 2.0 | 9.0 | 0.0 | 0.0 | 1.0 | 0.0 |
| 35 | 0.500 | 5.0 | 9.0 | 8.0 | 8.0 | 2.0 | 2.0 | 2.0 | 2.0 |
| | 0.250 | 6.0 | 7.0 | 6.0 | 8.0 | 2.0 | 2.0 | 3.0 | 2.0 |
| | 0.125 | 3.0 | 9.0 | 5.0 | 6.0 | 1.0 | 1.0 | 2.0 | 1.0 |
| 36 | 0.500 | 8.0 | 9.0 | 5.0 | 8.0 | 2.0 | 2.0 | 3.0 | 2.0 |
| | 0.250 | 5.0 | 8.0 | 5.0 | 8.0 | 2.0 | 1.0 | 3.0 | 2.0 |
| | 0.125 | 4.0 | 8.0 | 5.0 | 7.0 | 2.0 | 1.0 | 2.0 | 1.0 |
| 37 | 0.500 | 3.0 | 4.0 | 3.0 | 4.0 | 0.0 | 0.0 | 2.0 | 1.0 |
| | 0.250 | 2.0 | 3.0 | 2.0 | 3.0 | 1.0 | 0.0 | 2.0 | 1.0 |
| | 0.125 | 2.0 | 3.0 | 3.0 | 3.0 | 0.0 | 0.0 | 2.0 | 1.0 |
| 38 | 0.500 | 6.0 | 8.0 | 6.0 | 7.0 | 1.0 | 1.0 | 2.0 | 1.0 |
| | 0.250 | 4.0 | 5.0 | 4.0 | 6.0 | 1.0 | 1.0 | 2.0 | 1.0 |
| | 0.125 | 2.0 | 4.0 | 4.0 | 5.0 | 1.0 | 1.0 | 2.0 | 1.0 |
| 39 | 0.500 | 9.0 | 9.0 | 9.0 | 9.0 | 9.0 | 8.0 | 6.0 | 6.0 |
| | 0.250 | 9.0 | 9.0 | 8.0 | 9.0 | 9.0 | 9.0 | 5.0 | 6.0 |
| | 0.125 | 8.0 | 9.0 | 6.0 | 9.0 | 6.0 | 5.0 | 4.0 | 6.0 |
| 40 | 0.500 | 9.0 | 9.0 | 9.0 | 9.0 | 9.0 | 9.0 | 6.0 | 6.0 |
| | 0.250 | 9.0 | 9.0 | 9.0 | 9.0 | 9.0 | 8.0 | 6.0 | 6.0 |
| | 0.125 | 9.0 | 9.0 | 9.0 | 9.0 | 7.0 | 7.0 | 5.0 | 5.0 |
| 41 | 0.500 | 9.0 | 9.0 | 7.0 | 5.0 | 2.0 | 1.0 | 1.0 | 1.0 |
| | 0.250 | 9.0 | 9.0 | 6.0 | 4.0 | — | — | 1.0 | — |
| | 0.125 | 7.0 | 9.0 | 3.0 | 7.0 | — | — | 1.0 | — |
| 42 | 0.500 | 9.0 | 9.0 | 5.0 | 6.0 | 4.0 | 3.0 | 3.0 | 2.0 |
| | 0.250 | 9.0 | 9.0 | 6.0 | 9.0 | 2.0 | 2.0 | 2.0 | 1.0 |
| | 0.125 | 9.0 | 9.0 | 6.0 | 9.0 | — | — | 1.0 | — |
| 43 | 0.500 | 9.0 | 9.0 | 9.0 | 9.0 | 3.0 | 2.0 | 1.0 | 2.0 |
| | 0.250 | 9.0 | 9.0 | 9.0 | 8.0 | 2.0 | 2.0 | 1.0 | 1.0 |
| | 0.125 | 9.0 | 9.0 | 8.0 | 8.0 | 1.0 | 1.0 | 1.0 | — |

| Cpd. No. | Rate (kg/ha) | GLXMAW | ORYSA | TRZAWO | ZEAMX |
|---|---|---|---|---|---|
| 1 | 0.500 | 5.0 | 3.7 | 4.5 | 3.7 |
| | 0.250 | 5.0 | 2.3 | 4.5 | 2.3 |
| | 0.125 | 3.0 | 2.3 | 3.0 | 2.3 |
| 2 | 0.500 | 4.0 | 4.0 | 4.0 | 3.0 |
| | 0.250 | 4.0 | 4.0 | 4.0 | 3.0 |
| | 0.125 | 3.0 | 4.0 | 3.0 | 2.0 |
| 3 | 0.500 | 4.0 | 5.0 | 4.0 | 3.0 |
| | 0.250 | 4.0 | 5.0 | 4.0 | 3.0 |
| | 0.125 | 4.0 | 5.0 | 4.0 | 3.0 |
| 4 | 0.500 | 5.0 | 4.0 | 5.0 | 3.0 |
| | 0.250 | 5.0 | 3.0 | 3.0 | 3.0 |
| | 0.125 | 5.0 | 3.0 | 2.0 | 2.0 |
| 5 | 0.500 | 6.1 | 5.2 | 5.3 | 5.9 |
| | 0.250 | 6.0 | 4.7 | 4.9 | 4.8 |
| | 0.125 | 5.3 | 4.1 | 4.4 | 4.2 |
| 6 | 0.500 | 6.0 | 3.0 | 4.0 | 4.0 |
| | 0.250 | 5.0 | 2.0 | 3.0 | 3.0 |
| | 0.125 | 5.0 | 2.0 | 3.0 | 3.0 |
| 7 | 0.500 | 3.0 | 6.0 | 5.0 | 3.0 |
| | 0.250 | 3.0 | 6.0 | 5.0 | 3.0 |
| | 0.125 | 4.0 | 5.0 | 4.0 | 3.0 |
| 8 | 0.500 | 2.0 | 3.0 | 2.0 | 2.0 |
| | 0.250 | 2.0 | 3.0 | 2.0 | 3.0 |
| | 0.125 | 2.0 | 2.0 | 2.0 | 2.0 |
| 9 | 0.125 | 5.0 | 5.0 | 5.0 | 4.0 |
| 10 | 0.125 | 2.0 | 0.0 | 0.0 | 0.0 |
| 11 | 0.125 | 1.0 | 2.0 | 3.0 | 1.0 |
| 12 | 0.125 | 6.0 | 3.0 | 5.0 | 4.0 |
| 13 | 0.125 | 2.0 | 1.0 | 2.0 | 1.0 |
| 14 | 0.125 | 2.0 | 1.0 | 1.0 | 1.0 |
| 15 | 0.125 | 3.0 | 2.0 | 4.0 | 2.0 |
| 16 | 0.125 | 3.0 | 2.0 | 4.0 | 2.0 |
| 17 | 0.125 | 2.0 | 2.0 | 3.0 | 2.0 |
| 18 | 0.500 | 3.0 | 3.0 | 3.0 | 4.0 |
| | 0.250 | 3.0 | 3.0 | 3.0 | 3.0 |
| | 0.125 | 3.0 | 1.0 | 2.0 | 3.0 |
| 19 | 0.125 | 2.0 | 2.0 | 4.0 | 2.0 |
| 20 | 0.500 | 4.0 | 4.0 | 5.0 | 4.0 |
| | 0.250 | 4.0 | 3.0 | 4.0 | 4.0 |
| | 0.125 | 3.0 | 2.0 | 4.0 | 3.0 |
| 21 | 0.500 | 8.0 | 6.0 | 4.0 | 9.0 |
| | 0.250 | 5.0 | 5.0 | 4.0 | 9.0 |
| | 0.125 | 7.0 | 4.0 | 4.0 | 9.0 |
| 22 | 0.500 | 5.0 | 5.0 | 5.0 | 6.0 |
| | 0.250 | 5.0 | 5.0 | 5.0 | 4.0 |
| | 0.125 | 5.0 | 4.0 | 4.0 | 6.0 |
| 23 | 0.500 | 6.0 | 4.0 | 3.0 | 4.0 |
| | 0.250 | 7.0 | 4.0 | 4.0 | 5.0 |
| | 0.125 | 6.0 | 3.0 | 4.0 | 5.0 |
| 24 | 0.500 | 5.0 | 3.0 | 4.0 | 4.0 |

TABLE 1-continued
Postemergence Herbicidal Evaluations of Test Compounds

|   |       |     |     |     |     |
|---|-------|-----|-----|-----|-----|
|   | 0.250 | 4.0 | 2.0 | 3.0 | 3.0 |
|   | 0.125 | 4.0 | 2.0 | 3.0 | 4.0 |
| 25 | 0.500 | 4.8 | 2.8 | 3.3 | 4.0 |
|   | 0.250 | 4.3 | 2.8 | 3.5 | 3.5 |
|   | 0.125 | 4.0 | 2.8 | 3.8 | 3.5 |
| 26 | 0.500 | 5.0 | 4.0 | 4.0 | 5.0 |
|   | 0.250 | 5.0 | 3.0 | 3.0 | 5.0 |
|   | 0.125 | 4.0 | 2.0 | 3.0 | 3.0 |
| 27 | 0.500 | 4.0 | 2.0 | 3.0 | 4.0 |
|   | 0.250 | 4.0 | 2.0 | 3.0 | 4.0 |
|   | 0.125 | 3.0 | 1.0 | 2.0 | 3.0 |
| 28 | 0.500 | 4.0 | 3.0 | 3.0 | 3.0 |
|   | 0.250 | 4.0 | 2.0 | 2.0 | 3.0 |
|   | 0.125 | 3.0 | 2.0 | 2.0 | 3.0 |
| 29 | 0.500 | 4.0 | 4.0 | 4.0 | 4.0 |
|   | 0.250 | 3.0 | 4.0 | 4.0 | 4.0 |
|   | 0.125 | 3.0 | 3.0 | 3.0 | 4.0 |
| 30 | 0.500 | 4.0 | 2.0 | 3.0 | 3.0 |
|   | 0.250 | 3.0 | 2.0 | 3.0 | 3.0 |
|   | 0.125 | 2.0 | 2.0 | 2.0 | 3.0 |
| 31 | 0.500 | 5.0 | 3.0 | 4.0 | 5.0 |
|   | 0.250 | 5.0 | 3.0 | 4.0 | 5.0 |
|   | 0.125 | 4.0 | 2.0 | 2.0 | 4.0 |
| 32 | 0.500 | 2.0 | 1.0 | 2.0 | 3.0 |
|   | 0.250 | 2.0 | 1.0 | 2.0 | 3.0 |
|   | 0.125 | 1.0 | 1.0 | 1.0 | 3.0 |
| 33 | 0.500 | 2.0 | 1.0 | 1.0 | 3.0 |
|   | 0.250 | 2.0 | 1.0 | 1.0 | 3.0 |
|   | 0.125 | 1.0 | 1.0 | 1.0 | 3.0 |
| 34 | 0.500 | 1.0 | 1.0 | 2.0 | 3.0 |
|   | 0.250 | 1.0 | 1.0 | 2.0 | 3.0 |
|   | 0.125 | 1.0 | 1.0 | 2.0 | 3.0 |
| 35 | 0.500 | 2.0 | 1.0 | 2.0 | 3.0 |
|   | 0.250 | 2.0 | 1.0 | 2.0 | 3.0 |
|   | 0.125 | 2.0 | 1.0 | 2.0 | 3.0 |
| 36 | 0.500 | 3.0 | 1.0 | 3.0 | 3.0 |
|   | 0.250 | 2.0 | 1.0 | 3.0 | 3.0 |
|   | 0.125 | 2.0 | 1.0 | 2.0 | 3.0 |
| 37 | 0.500 | 1.0 | 1.0 | 1.0 | 1.0 |
|   | 0.250 | 1.0 | 1.0 | 1.0 | 1.0 |
|   | 0.125 | 1.0 | 1.0 | 1.0 | 1.0 |
| 38 | 0.500 | 3.0 | 3.0 | 4.0 | 4.0 |
|   | 0.250 | 3.0 | 3.0 | 4.0 | 3.0 |
|   | 0.125 | 2.0 | 1.0 | 2.0 | 3.0 |
| 39 | 0.500 | 4.0 | 4.0 | 5.0 | 5.0 |
|   | 0.250 | 4.0 | 3.0 | 5.0 | 5.0 |
|   | 0.125 | 4.0 | 2.0 | 4.0 | 4.0 |
| 40 | 0.500 | 8.0 | 6.0 | 6.0 | 8.0 |
|   | 0.250 | 9.0 | 5.0 | 7.0 | 8.0 |
|   | 0.125 | 8.0 | 4.0 | 5.0 | 6.0 |
| 41 | 0.500 | 1.0 | 1.0 | 2.0 | 2.0 |
|   | 0.250 | 2.0 | 1.0 | 1.0 | 2.0 |
|   | 0.125 | 1.0 | 1.0 | 1.0 | 2.0 |
| 42 | 0.500 | 2.0 | 2.0 | 3.0 | 2.0 |
|   | 0.250 | 2.0 | 2.0 | 3.0 | 2.0 |
|   | 0.125 | 1.0 | 1.0 | 2.0 | 2.0 |
| 43 | 0.500 | 3.0 | 3.0 | 3.0 | 2.0 |
|   | 0.250 | 3.0 | 2.0 | 3.0 | 2.0 |
|   | 0.125 | 2.0 | 2.0 | 2.0 | 2.0 |

EXAMPLE 26

Preemergence herbicidal evaluation of test compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.125 to 0.50 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 25.

The data obtained are reported in Table II below. The compounds evaluated are reported by compound number given in Example 25.

TABLE II
Preemergence Herbicidal Evaluations of Test Compounds

| Cpd. No. | Rate (kg/ha) | ABUTH | AMARE | AMBEL | IPOHE | DIGSA | ECHCG | PANMIY | SETVI |
|---|---|---|---|---|---|---|---|---|---|

TABLE II-continued

Preemergence Herbicidal Evaluations of Test Compounds

| Cpd. No. | Rate (kg/ha) | | | | | | | |
|---|---|---|---|---|---|---|---|---|
| 1 | 0.500 | 8.3 | 9.0 | 8.7 | 8.5 | 8.5 | 5.5 | 2.0 | 8.3 |
| 2 | 0.500 | 9.0 | 9.0 | 9.0 | 5.0 | 8.0 | 2.0 | 5.0 | 5.0 |
| 3 | 0.500 | 9.0 | 9.0 | 8.0 | 9.0 | 9.0 | 3.0 | 6.0 | 9.0 |
| 4 | 0.500 | 8.0 | 9.0 | 5.0 | 5.0 | 7.0 | 2.0 | 0.0 | 6.0 |
| 5 | 0.500 | 9.0 | 9.0 | 8.8 | 8.6 | 8.6 | 4.8 | 7.3 | 8.1 |
| 6 | 0.500 | 9.0 | 9.0 | 9.0 | 6.0 | 6.0 | 0.0 | 0.0 | 0.0 |
| 7 | 0.500 | 6.0 | 9.0 | 9.0 | 9.0 | 9.0 | 0.0 | 8.0 | 8.0 |
| 8 | 0.500 | 0.0 | 0.0 | 0.0 | 0.0 | 0.0 | 0.0 | 0.0 | 0.0 |
| 9 | 0.125 | 4.0 | 9.0 | 4.0 | 2.0 | 4.0 | 0.0 | 0.0 | 0.0 |
| 10 | 0.125 | 0.0 | 0.0 | 0.0 | 0.0 | 0.0 | 0.0 | 0.0 | 0.0 |
| 11 | 0.125 | 2.0 | 8.0 | 2.0 | 0.0 | 0.0 | 0.0 | 0.0 | 0.0 |
| 12 | 0.125 | 5.0 | 9.0 | 7.0 | 0.0 | 0.0 | 0.0 | 0.0 | 0.0 |
| 13 | 0.125 | 0.0 | 0.0 | 0.0 | 0.0 | 0.0 | 0.0 | 0.0 | 0.0 |
| 14 | 0.125 | 0.0 | 0.0 | 0.0 | 0.0 | 0.0 | 0.0 | 0.0 | 0.0 |
| 15 | 0.125 | 0.0 | 0.0 | 0.0 | 0.0 | 0.0 | 0.0 | 0.0 | 0.0 |
| 16 | 0.125 | 0.0 | 0.0 | 0.0 | 0.0 | 0.0 | 0.0 | 0.0 | 0.0 |
| 17 | 0.125 | 0.0 | 0.0 | 0.0 | 0.0 | 0.0 | 0.0 | 0.0 | 0.0 |
| 18 | 0.500 | 5.0 | 9.0 | 0.0 | 0.0 | 2.0 | 2.0 | 0.0 | 2.0 |
| 19 | 0.125 | 0.0 | 0.0 | 0.0 | 0.0 | 0.0 | 0.0 | 0.0 | 0.0 |
| 20 | 0.500 | 5.0 | 9.0 | 5.0 | 6.0 | 9.0 | 2.0 | 0.0 | 6.0 |
| 21 | 0.500 | 0.0 | 9.0 | 5.0 | 9.0 | 6.0 | 5.0 | 0.0 | 0.0 |
| 22 | 0.500 | 5.0 | 9.0 | 6.0 | 5.0 | 7.0 | 0.0 | 0.0 | 0.0 |
| 23 | 0.500 | 9.0 | 9.0 | 8.0 | 5.0 | 8.0 | 0.0 | 2.0 | 0.0 |
| 24 | 0.500 | 2.0 | 2.0 | 0.0 | 2.0 | 0.0 | 0.0 | 0.0 | 0.0 |
| 25 | 0.500 | 8.0 | 9.0 | 7.0 | 3.0 | 2.7 | 1.0 | 1.0 | 2.0 |
| 26 | 0.500 | 2.0 | 2.0 | 0.0 | 3.0 | 0.0 | 2.0 | 5.0 | 0.0 |
| 27 | 0.500 | 2.0 | 0.0 | 0.0 | 5.0 | 5.0 | 2.0 | 4.0 | 3.0 |
| 28 | 0.500 | 2.0 | 9.0 | 5.0 | 2.0 | 0.0 | 0.0 | 0.0 | 0.0 |
| 29 | 0.500 | 0.0 | 9.0 | 2.0 | 9.0 | 0.0 | 0.0 | 0.0 | 0.0 |
| 30 | 0.500 | 0.0 | 0.0 | 0.0 | 0.0 | 0.0 | 0.0 | 0.0 | 0.0 |
| 31 | 0.500 | 9.0 | 9.0 | 0.0 | 0.0 | 2.0 | 2.0 | 0.0 | 0.0 |
| 32 | 0.500 | 0.0 | — | 0.0 | — | 0.0 | 0.0 | — | 0.0 |
| 33 | 0.500 | 0.0 | — | 0.0 | — | 0.0 | 0.0 | — | 0.0 |
| 34 | 0.500 | 0.0 | — | 0.0 | — | 0.0 | 0.0 | — | 0.0 |

| Cpd. No. | Rate (kg/ha) | GLXMAW | ORYSA | TRZAWO | ZEAMX |
|---|---|---|---|---|---|
| 1 | 0.500 | 0.0 | 0.0 | 0.0 | 1.0 |
| 2 | 0.500 | 0.0 | 0.0 | 3.0 | 0.0 |
| 3 | 0.500 | 3.0 | 0.0 | 3.0 | 0.0 |
| 4 | 0.500 | 0.0 | 0.0 | 0.0 | 0.0 |
| 5 | 0.500 | 7.0 | 2.1 | 2.1 | 2.6 |
| 6 | 0.500 | 2.0 | 0.0 | 3.0 | 0.0 |
| 7 | 0.500 | 0.0 | 3.0 | 2.0 | 0.0 |
| 8 | 0.500 | 0.0 | 0.0 | 0.0 | 0.0 |
| 9 | 0.125 | 0.0 | 0.0 | 0.0 | 0.0 |
| 10 | 0.125 | 0.0 | 0.0 | 0.0 | 0.0 |
| 11 | 0.125 | 0.0 | 0.0 | 0.0 | 0.0 |
| 12 | 0.125 | 0.0 | 0.0 | 0.0 | 0.0 |
| 13 | 0.125 | 0.0 | 0.0 | 0.0 | 0.0 |
| 14 | 0.125 | 0.0 | 0.0 | 0.0 | 0.0 |
| 15 | 0.125 | 0.0 | 0.0 | 0.0 | 0.0 |
| 16 | 0.125 | 0.0 | 0.0 | 0.0 | 0.0 |
| 17 | 0.125 | 0.0 | 0.0 | 0.0 | 0.0 |
| 18 | 0.500 | 2.0 | 0.0 | 0.0 | 0.0 |
| 19 | 0.125 | 0.0 | 0.0 | 0.0 | 0.0 |
| 20 | 0.500 | 0.0 | 0.0 | 0.0 | 0.0 |
| 21 | 0.500 | 0.0 | 0.0 | 0.0 | 0.0 |
| 22 | 0.500 | 0.0 | 0.0 | 0.0 | 0.0 |
| 23 | 0.500 | 1.0 | 3.0 | 2.0 | 0.0 |
| 24 | 0.500 | 0.0 | 0.0 | 0.0 | 0.0 |
| 25 | 0.500 | 4.5 | 0.0 | 0.0 | 0.5 |
| 26 | 0.500 | 0.0 | 3.0 | 2.0 | 0.0 |
| 27 | 0.500 | 0.0 | 2.0 | 2.0 | 0.0 |
| 28 | 0.500 | 0.0 | 0.0 | 0.0 | 0.0 |
| 29 | 0.500 | 0.0 | 0.0 | 0.0 | 0.0 |
| 30 | 0.500 | 0.0 | 0.0 | 0.0 | 0.0 |
| 31 | 0.500 | 0.0 | 0.0 | 0.0 | 0.0 |
| 32 | 0.500 | — | — | — | — |
| 33 | 0.500 | — | — | — | — |
| 34 | 0.500 | — | — | — | — |

EXAMPLE 27

Rice tolerance to post-transplant applications and preemergence weed control under flooded paddy conditions The tolerance of transplanted rice to post-transplanted herbicide applications is determined as follows: Two ten-day-old rice seedlings (CV. Tebonnet) are transplanted into a silt loam soil in 32 oz plastic containers with a diameter of 10.5 cm and no drainage holes. After transplanting the containers are flooded and the water level is maintained at 1.5 to 3 cm above the soil surface. Three days after transplanting, the flooded soil surface of the containers is treated with the selected aqueous/acetone 50/50 v/v mixture containing the test compounds to provide the equivalent of 1.0, 0.5 and 0.25 kg/ha of active ingredient. The treated containers are placed on greenhouse benches, watered such that the water level is maintained as stated above, and cared for according to normal greenhouse procedures. Three to four weeks after treatment the test is terminated and each container is examined and herbicidal effect rated according to the rating system provided in Example 25. The data obtained are reported in Table III.

Preemergence herbicidal activity under flooded paddy conditions on barnyardgrass is determined as follows: Barnyardgrass seeds are planted in the top 0.5 cm of silt loam soil in 32 oz plastic containers with a diameter of 10.5 cm and no drainage holes. Water is added to these containers and maintained at 1.5 to 3 cm above the soil surface for the duration of the experiment. The test compounds are applied as an aqueous-/acetone mixture 50/50 v/v pipetted directly into the flood water to give the equivalent of 1.0, 0.5 and 0.25 kg/ha of active ingredient. The treated containers are placed on greenhouse benches and cared for according to normal greenhouse procedures. Three to four weeks after treatment the test is terminated and each container is examined and herbicidal effect rated according to the rating system provided in Example 25. The data obtained are reported in Table III.

TABLE III

PADDY CONDITIONS - POST-TRANSPLANT RICE PREEMERGENCE BARNYARDGRASS

| Compound | Rate (kg/ha) | BARNYARD GRASS | RICE |
|---|---|---|---|
| Methyl {o-[5-(2,4-dichloro- | 1.00 | 9.0 | 2.0 |
| phenoxy)-2-nitrophenoxy]- | 0.50 | 9.0 | 1.5 |
| phenoxy}acetate | 0.25 | 9.0 | 1.0 |

As can be seen from the data in Table III, methyl {o-[5-(2,4-dichlorophenoxy) -2-nitrophenoxy]phenoxy-}acetate is useful for the preemergence control of barnyardgrass in the presence of transplanted paddy rice.

What is claimed is:

1. A compound methyl {o-{5-[(2-chloro-$\alpha,\alpha,\alpha$,6-tetrafluoro-p-tolyl)-oxy]-2-nitrophenoxy}phenoxy}acetate.

2. A herbicidal composition which comprises an inert solid or liquid carrier and a herbicidally effective amount of a compound methyl {o-{5-[(2-chloro-$\alpha,\alpha,\alpha$,6-tetrafluoro-p-tolyl)-oxy]-22-nitrophenoxy}phenoxy}acetate.

* * * * *